(12) United States Patent
Le

(10) Patent No.: US 12,116,598 B2
(45) Date of Patent: Oct. 15, 2024

(54) THYMIC EPITHELIAL CELLS, EXOSOMES DERIVED THEREFROM, AND METHODS OF MAKING AND USING SAME

(71) Applicant: LOYOLA UNIVERSITY OF CHICAGO, Chicago, IL (US)

(72) Inventor: Phong Le, Western Springs, IL (US)

(73) Assignee: LOYOLA UNIVERSITY OF CHICAGO, Chicago, IL (US)

( * ) Notice: Subject to any disclaimer, the term of this patent is extended or adjusted under 35 U.S.C. 154(b) by 913 days.

(21) Appl. No.: 16/823,737

(22) Filed: Mar. 19, 2020

(65) Prior Publication Data

US 2020/0299641 A1    Sep. 24, 2020

Related U.S. Application Data

(60) Provisional application No. 62/820,930, filed on Mar. 20, 2019.

(51) Int. Cl.
| | |
|---|---|
| *C12N 5/10* | (2006.01) |
| *C07K 14/475* | (2006.01) |
| *C07K 14/705* | (2006.01) |
| *C12N 5/078* | (2010.01) |
| *C12N 5/0783* | (2010.01) |
| *G01N 33/569* | (2006.01) |

(52) U.S. Cl.
CPC .............. *C12N 5/10* (2013.01); *C07K 14/475* (2013.01); *C07K 14/705* (2013.01); *C12N 5/0636* (2013.01); *C12N 5/065* (2013.01); *G01N 33/56966* (2013.01); *C12N 2506/11* (2013.01); *C12N 2510/00* (2013.01)

(58) Field of Classification Search
None
See application file for complete search history.

(56) References Cited

PUBLICATIONS

Andrawes et al. JBC 288: 25477-25489 (Year: 2013).*
Beaudette-Zlatanova et al. Ex. Hematol. 39: 570-579 (Year: 2011).*
De Smedt et al., Human bone marrow CD34+ progenitor cells mature to T cells on OP9-DL1 stromal cell line without thymus microenvironment, Blood Cells Mol. Dis., 33:227-232 (2004).
Denning et al., Human thymic epithelial cells directly induce activation of autologous immature thymocytes, Proc. Natl. Acad. Sci. USA., 85:3125-3129 (1988).
Haddad et al., Molecular characterization of early human T/NK and B-lymphoid progenitor cells in umbilical cord blood, Blood, 104:3918-3926 (2004).
Haynes et al., Human intrathymic T cell differentiation, Semin Immunol., 2:67-77 (1990).
Jaleco et al., Differential effects of Notch ligands Delta-1 and Jagged-1 in human lymphoid differentiation, J. Exp. Med., 194:991-1002 (2001).
Karanu et al., Human homologues of Delta-1 and Delta-4 function as mitogenic regulators of primitive human hematopoietic cells, Blood, 97:1960-1967 (2001).
Lehninger, Biochemistry, 2nd Edition; Worth Publishers, Inc., New York, pp. 71-77 (1975).
Lundberg et al., Thymic exosomes promote the final maturation of thymocytes, Sci. Rep., 6:36479 (2016).
Markert et al., Transplantation of thymus tissue in complete DiGeorge syndrome, N. Engl. J. Med., 341:1180-1189 (1999).
Miller, Effect of thymectomy in adult mice on immunological responsiveness, Nature, 208:1337-1338 (1965).
Miller, Immunological function of the thymus, Lancet., 2:748-749 (1961).
Mohtashami et al., Direct comparison of Dll1- and Dll4-mediated Notch activation levels shows differential lymphomyeloid lineage commitment outcomes, J. Immunol., 185:867-876 (2010).
Motte-Mohs et al., Induction of T-cell development from human cord blood hematopoietic stem cells by Delta-like 1 in vitro, Blood, 105:1431-1439 (2005).
Nehls et al., New member of the winged-helix protein family disrupted in mouse and rat nude mutations, Nature, 372:103-107 (1994).
Pignata et al., Human equivalent of the mouse Nude/SCID phenotype: long-term evaluation of immunologic reconstitution after bone marrow transplantation, Blood, 97:880-885 (2001).
Pui et al., Notch1 expression in early lymphopoiesis influences B versus T lineage determination, Immunity, 11:299-308 (1999).
Radtke et al., Deficient T cell fate specification in mice with an induced inactivation of Notch1, Immunity, 10:547-558 (1999).
Schluns et al., Human thymic epithelial cells produce TGF-beta 3 and express TGF-beta receptors, Int. Immunol., 7:1681-1690 (1995).
Schmitt et al., Induction of T cell development from hematopoietic progenitor cells by delta-like-1 in vitro, Immunity, 17:749-756 (2002).
Shah et al., Notch receptor-ligand interactions during T cell development, a ligand endocytosis-driven mechanism, Curr. Top. Microbiol. Immunol., 360:19-46 (2012).
Sheldon et al., New mechanism for Notch signaling to endothelium at a distance by Delta-like 4 incorporation into exosomes, Blood, 116:2385-2394 (2010).
Skogberg et al., Human thymic epithelial primary cells produce exosomes carrying tissue-restricted antigens, Immunol. Cell Biol., 93:727-734 (2015).
Spits, Development of alphabeta T cells in the human thymus, Nature Rev. Immunol., 2:760-772 (2002).

\* cited by examiner

*Primary Examiner* — Michael D Pak
(74) *Attorney, Agent, or Firm* — MARSHALL, GERSTEIN & BORUN LLP

(57) ABSTRACT

The present disclosure provides engineered thymic epithelial cells and cell lines, as well as extracellular vesicles derived therefrom. The disclosure also provides exosomes that display specific surface proteins, and provides methods for using said materials for treating subjects and for identifying cells.

8 Claims, 15 Drawing Sheets

THYMIC EPITHELIAL CELLS, EXOSOMES DERIVED THEREFROM, AND METHODS OF MAKING AND USING SAME

CROSS-REFERENCE TO RELATED APPLICATIONS

This Application claims the benefit of U.S. Provisional Application 62/820,930 filed on Mar. 20, 2019. The entire contents of these applications are incorporated herein by reference in their entirety.

STATEMENT REGARDING FEDERALLY SPONSORED RESEARCH

The invention was made with Government support under Grant Nos. AG023809 awarded by the NIH. The government has certain rights in the invention.

BACKGROUND

The present invention generally relates to human T cell generation. The invention particularly relates to the methods for generating human thymic epithelial cells and exosomes derived therefrom for use in producing human T cells from human hematopoietic stem cells.

The thymus is the primary lymphoid organ in humans that is essential for the development of T cells from the homing hematopoietic stem cells (HSCs) which are derived from the bone marrow. Within the thymus, thymic epithelial cells (TECs) are the stromal cells whose primary function is to provide a critical signal and growth factors to initiate and promote the development of T cells from HSCs. It would be desirable if methods and compositions were available for promoting human T cell development, mainly using TECs or TEC-derived exosomes.

SUMMARY OF THE INVENTION

In various aspects, the present disclosure provides engineered thymic epithelial cells and cell lines, as well as extracellular vesicles derived therefrom. The disclosure also provides exosomes that display specific surface proteins, and provides methods for using said materials for treating subjects and for identifying cells.

In one embodiment, the present disclosure provides an isolated human thymic epithelial cell comprising at least one expression vector encoding a human Delta-like 4 gene (DLL4). In a related embodiment, the expression vector is capable of expressing a Delta-like 4 protein. In another embodiment, the Delta-like 4 protein amino acid sequence is the natural human amino acid sequence or is a fragment, analog or derivative of the natural human amino acid sequence.

In another embodiment of the disclosure, an isolated human thymic epithelial cell comprising at least one expression vector encoding a human WNT3A gene (WNT3A) is provided. In a related embodiment, the expression vector is capable of expressing a Wnt-3a protein. In another embodiment, the Wnt-3a protein amino acid sequence is the natural human amino acid sequence or is a fragment, analog or derivative of the natural human amino acid sequence.

Still another embodiment of the present disclosure provides an aforementioned cell wherein the cell is a genetically modified cell from cell line TEC84. In other embodiments, a collection of cells comprising a cell line comprised of isolated human thymic epithelial cell according to the aforementioned embodiments, is provided. Further, a composition comprising the collection of cells is also provided.

Extracellular vesicles such as exosomes are provided in various embodiments. In one embodiment, an isolated exosome derived from a human thymic epithelial cell is provided, wherein the exosome displays human Delta-like 4 protein on its membrane surface. In another embodiment, the Delta-like 4 protein amino acid sequence is the natural human amino acid sequence or is a fragment, analog or derivative of the natural human amino acid sequence. In another embodiment, an isolated exosome derived from a human thymic epithelial cell, wherein the exosome displays human Wnt-3a protein on its membrane surface, is provided. In another embodiment, the Wnt-3a protein amino acid sequence is the natural human amino acid sequence or is a fragment, analog or derivative of the natural human amino acid sequence. In still another embodiment, a collection of exosomes derived from an aforementioned cell line comprised of isolated human thymic epithelial cells is provided. In yet another embodiment, a composition comprising the collection of exosomes is provided.

In embodiment of the present disclosure, a method of stimulating production of a T cell from a hematopoietic stem cell is provided, the method comprising the steps of: (a) contacting a hematopoietic stem cell expressing a Notch receptor and with an exosome derived from a human thymic epithelial cell, the exosome displaying a human Delta-like 4 protein, wherein the Delta-like 4 protein amino acid sequence is the natural human amino acid sequence or is a fragment, analog or derivative of the natural human amino acid sequence; or (b) contacting a hematopoietic stem cell with an exosome derived from a human thymic epithelial cell, the exosome displaying a human Wnt-3a protein, wherein the Wnt-3a protein amino acid sequence is the natural human amino acid sequence or is a fragment, analog or derivative of the natural human amino acid sequence; or (c) both steps (a) and (b).

In another embodiment, the contacting occurs in vivo following administration of the exosome or exosomes to a patient in need thereof. In still another embodiment, the administration occurs in bone marrow, thymus, liver, and mucosa tissues such as the gastrointestinal tract. In yet another embodiment, the contacting occurs ex vivo following administration of the exosome or exosomes to a composition comprising a sample taken from patient, said sample comprising umbilical cord blood hematopoietic stem cells, mobilized adult peripheral stem cells, and bone marrow hematopoietic stem cells.

In another embodiment, the T cell expresses one or more cell surface marker selected from the group consisting of CD7, CD3, CD4, and CD8. In still another embodiment, the hematopoietic stem cell expresses one or more cell surface marker selected from the group consisting of CD34, CD7 CD127, CD62L CCR9, CCR7, and CXCR4.

The present disclosure also provides a method of identifying a subpopulation of hematopoietic stem cells expressing a Notch receptor and capable of developing into T cells, comprising the steps of: (a) contacting a hematopoietic stem cell expressing a Notch receptor and with an exosome derived from a human thymic epithelial cell, the exosome displaying a human Delta-like 4 protein on its membrane surface, wherein the Delta-like 4 protein amino acid sequence is the natural human amino acid sequence or is a fragment, analog or derivative of the natural human amino acid sequence; (b) contacting the exosome of (a) with an antibody or antigen-binding fragment thereof specific for the Delta-like 4 protein; and (c) determining the presence of an exosome bound to a hematopoietic stem cell expressing a Notch receptor and an antibody of (b); wherein the subpopulation of hematopoietic stem cells expresses one or more cell surface marker selected from the group consisting of CD34, CD7, CD127, CD62L, CCR9, CCR7, and CXCR4, and wherein the subpopulation is from a sample population of hematopoietic stem cells collected from a source selected from the group consisting of umbilical cord blood stem cells, adult peripheral blood hematopoietic stem cells, and bone marrow hematopoietic stem cells. In another embodiment, the subpopulation of hematopoietic stem cells expresses each of CD34, CD7, CD127, CD62L, CCR9, CCR7, and CXCR4.

A method of treating X-linked severe combined immunodeficiencies (X-SCIDs), Wiskott-Aldrich syndrome, ataxia telangiectasia, DiGeorge syndrome (22q11.2 deletion syndrome), immuno-osseous dysplasias, dyskeratosis congenita, and chronic mucocutaneous candidiasis, Omenn syndrome, CD40L deficiency, ADA-deficiency and hematopoietic stem cell transplant for hematologic malignancy diseases is provided in one embodiment, the method comprising administering to a subject in need thereof (i) a therapeutic composition comprising an aforementioned cell, or (ii) a therapeutic composition comprising an aforementioned exosome, or both (i) and (ii).

In another embodiment, the disclosure provides a method of treating X-linked severe combined immunodeficiencies (X-SCIDs), Wiskott-Aldrich syndrome, ataxia telangiectasia, DiGeorge syndrome (22q11.2 deletion syndrome), immuno-osseous dysplasias, dyskeratosis congenita, and chronic mucocutaneous candidiasis, Omenn syndrome, CD40L deficiency, ADA-deficiency and hematopoietic stem cell transplant for hematologic malignancy diseases, the method comprising (a) obtaining a sample from a subject, the sample comprising umbilical cord blood stem cells, adult peripheral stem cells, and bone marrow stem cells; (b) contacting the sample of (a) with (i) a composition comprising an aforementioned cell, or (ii) a composition comprising an aforementioned exosome, or both (i) and (ii), under conditions that allow production of T cells; and (c) administering a composition comprising T cells produced in step (b) to the subject.

In still another embodiment, a method of identifying T cells capable of binding a major histocompatibility complex (MHC)-peptide complex is provided comprising the steps of: (a) introducing a peptide or an expression vector capable of expressing the peptide into a human thymic epithelial cell; (b) obtaining an exosome from the human thymic epithelial cell of (a), wherein the exosome is capable of presenting the peptide as part of a MHC-peptide complex; (c) contacting the exosome of step (b) with a composition comprising T cells under conditions that allow said MHC-peptide complex to contact a T cell receptor on said T cells; and (d) identifying T cells capable of binding said exosome displaying said MHC-peptide complex. In another embodiment, the MHC is class I or II. In yet another embodiment, the human thymic epithelial cell is a cell from cell line TEC84.

Additional aspects of the present disclosure are as follows. In one aspect, an isolated human thymic epithelial cell line modified to incorporate the human Delta-like 4 gene into the expression vector thereof is provided. In another aspect, an isolated exosome derived from the aforementioned cell and having the Delta-like 4 membrane ligand is provided. In still another aspect, a method is provided comprising: providing a culture of isolated human thymic epithelial cells modified to incorporate the human Delta-like 4 gene into the expression vector thereof; and isolating exosomes from the culture that have the Delta-like 4 membrane ligand. In one aspect, the method further comprises contacting the exosomes with hematopoietic stem cells in order to cause Notch signaling and thereby induce development of T cells from the hematopoietic stem cells.

In an additional aspect of the present disclosure, an isolated human thymic epithelial cell line modified to incorporate the WNT3A gene into the expression vector thereof is provided. In another aspect, an isolated exosome derived from the cell of claim 5 and having the WNT3A membrane ligand. In still another aspect, the isolated exosome derived from the aforementioned cell and an assay configured to detect $CD34^+$ HSCs having Notch receptors capable of engaging with Exo DLL4 is provided.

Other aspects and advantages of this invention will be further appreciated from the following detailed description.

BRIEF DESCRIPTION OF THE DRAWINGS

FIG. 6 shows that the Jurkat DMF5-TCR T cells bound to exosomes isolated from TEC-HLA-A2 loaded with MART-1 peptide. From left to right: CD3 to detect T cells; merging of CD3 and HLA-A2; merging of CD34 (DMF5 TCR) and HLA-A2; CD34; bright field; HLA-A2.

DETAILED DESCRIPTION OF THE INVENTION

Figure 1:
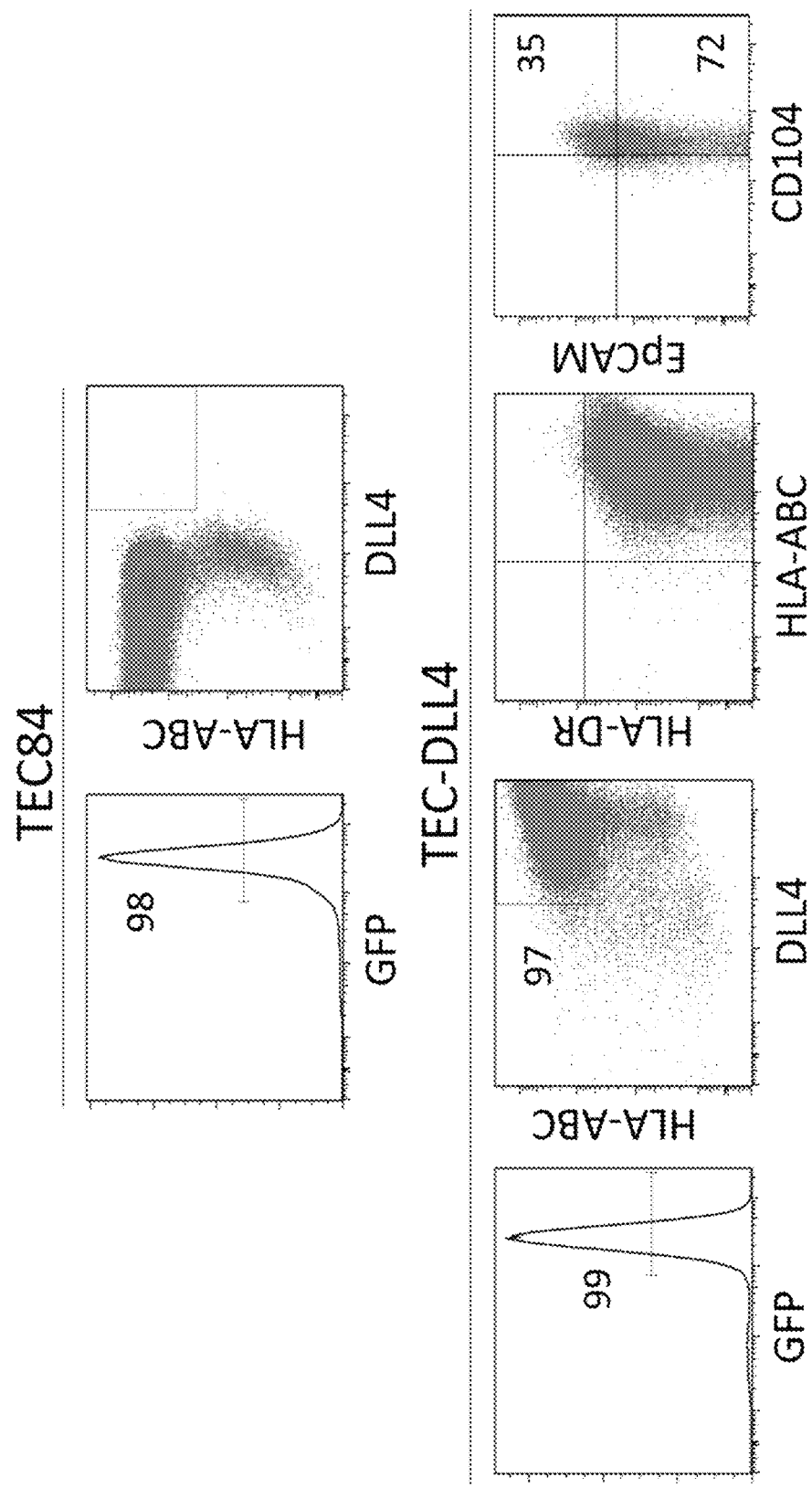
FIG. 1 shows plots representing data collected using flow cytometric analysis of human thymic epithelial cells that overexpress human cell surface ligand Delta-like 4 (TEC-DLL4). Top two panels are controls with TEC84 transduced with the MigR1-GFP. The cells are positive for GFP (Top Left), and HLA- A,B,C (Top Right). Lower panels show the characteristics of the established TEC-DDL4 transduced with the MigR1-DLL4-GFP construct. The data depict the expression of GFP (Far Left), DLL4 and HLA- A,B,C (Center Left), HLA A.B. C and HLA-DR (Center Right) and CD104 and EpCAM, the markers for epithelial cells (Far Right). The numbers represent the percentage of positive cells.

The thymus is essential for the development of T cells from bone marrow-derived hematopoietic stem cells (HSCs) in animals and humans (Miller J. F., Lancet. 1961; 2:748-749; Miller J.F., Nature, 1965; 208:1337-1338; and Markert M L, et al., N Engl J Med. 1999; 341:1180-1189). Genetic and functional studies show that thymic epithelial cells (TECs) play a critical role in T cell development (Denning S M, et al., Proc Natl Acad Sci USA. 1988; 85:3125-3129; Haynes B F, et al., Semin Immunol. 1990; 2:67-77; Nehls M, et al., Nature. 1994; 372:103-107; and Pignata C, et al., Blood. 2001; 97:880-885). Phenotype analyses of ex vivo human thymocytes have revealed distinct stages of T cell maturation. The stages of T cell development in the thymus have been defined as HSC ($CD34^{pos}CD7^{neg}CD1a^{neg}$), preT/natural killer ($CD34^{POS}CD7^{pos}CD1a^{neg}$), preT ($CD34^{pos/lo}CD^{pos}CD1a^{pos}$), immature single positive ($CD1a^{pos}CD7^{pos}CD4^{pos}$), early double positive ($CD3^{neg}CD4^{pos}CD8^{pos}$), double positive (DP) ($CD3^{pos}CD4^{pos}CD8^{pos}$), and single positive (SP) ($CD3^{pos}CD4^{pos}CD8^{neg}$ or $CD3^{pos}CD8^{pos}CD4^{neg}$) (Spits H., Nature Rev Immunol. 2002; 2:760-772).

Notch signaling is essential for T cell lineage commitment and differentiation (Radtke F, et al., Immunity. 1999; 10:547-558; and Pui J C, et al., Immunity. 1999; 11:299-308); however, it is unclear which of the Notch ligands expressed by TEC trigger the physiological signal for T cell lineage commitment and/or maturation. Delta-like 4 (D14) and Delta-like 1 (D11) are both known to bind the receptor Notch-1 on HSC (Karanu F N, et al., Blood. 2001; 97:1960-1967). Murine BM stromal cell lines such as S17-DL1 and OP9-DL1 that overexpress the Notch ligand D11 and OP9-DL4 that overexpresses the Notch ligand D14 support T cell development from human cord blood (CB) HSCs (Jaleco A C, et al., J Exp Med. 2001; 194:991-1002; Haddad R, et al., Blood. 2004; 104:3918-3926; and La Motte-Mohs R N, et al., Blood. 2005; 105:1431-1439) and bone marrow (BM) HSCs (De Smedt M, et al., Blood Cells Mol Dis. 2004; 33:227-232) as well as murine HSCs (Schmitt T M, and Zuniga-Pflucker J C., Immunity. 2002; 17:749-756; and Mohtashami M, et al., J Immunol. 2010; 185:867-876).

As described herein, the present disclosure provides, in various aspects, genetically engineered TEC cell lines, e.g., with expression vectors comprising DLL4 and WNT3A, as well as TEC-derived exosomes with functional DLL4 and WNT3A. Various therapeutic applications of the exosomes in a cell-free platform system to promote T cell development include: treating patients with severe immunodeficiency diseases such as DiGeorge syndrome or FOXN1 mutation; treating patients who undergo hematopoietic stem cell transplant as a component of therapy for hematologic malignancy diseases, as well as other diseases and disorders as described herein.

A first culture system to take advantage of the Notch signaling pathway to promote T lineage commitment and development is the OP9-DL1 was described previously (T. M. Schmitt and J. C. Zuniga-Pflucker, Immunity. 17, 749-756 (2002)). The OP9 cell line was derived from mouse bone marrow and the Notch ligand DL1 was also murine origin. A cell-free culture system using soluble ligand was also developed to promote T cell development in vitro; however, the system is less efficient because Notch and its ligand interaction is only optimal when the ligand is membrane bound (Shah D. K. and J. C. ZunigaPflucker, Curr. Top. Microbiol. Immunol. 360, 19-46 (2012)). It was demonstrated that the physical contraction of the cell membrane provides a pulling physical force to generate the active intracellular component of the Notch receptor which acts as a transcriptional activator to induce transcription of Notch-dependent target genes.

While the clinical applications of exosomes is currently a focus of many laboratories, there is no system exists in which thymic epithelial cell-derived exomes with membrane DLL4 are utilized to promote human T cell development. However, exosomes have been shown produced by primary human thymic epithelial cells in vitro, and that thymic-derived exosomes affect the final stage of thymocyte maturation. Also, exosomes with DLL4 from endothelial cells have been shown to affect blood vessels formation (Skogberg G et al., Immunol. Cell Biol. 93, 727-734 (2015); Lundberg V et al., Sci. Rep. 6, 36479 (2016); and Sheldon H et al., Blood. 116, 2385-2394 (2010)).

The use of exosomes as a cell-free platform makes them available on-demand without requiring an extended time needed to grow cells as in the current cell-based system. Exosomes have been shown in vivo to display poor allogeneic response, thus reducing the potential to mediate an immune rejection response when given to patients. Exosomes are natural biological materials present in body fluids, display a short half-life and are readily eliminated through the renal system.

As described herein, in one aspect the Exo-DLL4 is directly introduced into the bone marrow to promote extrathymic T cell development. This approach is of clinically relevant given that most cancer patients are with advanced age; in such individual, thymic functions decline with age and are altered caused by chemotherapy. Because of the specific interaction between the Notch receptor and ExoDLL4, the exosomes, in other aspects of the present disclosure, are used to deliver cargo to a cell in a specific manner.

Peptides and polypeptides, as well as fragments, analogs and derivatives thereof, are contemplated as described herein. For example, in one aspect of the present disclosure, an exosome is loaded with an antigenic peptide for processing and display on the exosome surface in the context of a MHC. In another aspect, a Delta-like 4 protein and/or a Wnt-3a protein are expressed from an expression vector or vectors that have been introduced into a cell, e.g., a human thymic epithelial cell, and/or an exosome derived from such a cell. As described herein, the term protein or polypeptide or peptide refers to any proteinaceous molecule which exhibits biological activity that is associated with the protein or which exhibits antigenic determinants consistent with a full length molecule.

Protein molecules contemplated include full-length proteins, precursors of full length proteins, biologically active subunits or fragments of full length proteins, as well as biologically active derivatives and variants of any of these forms of proteins. Thus, therapeutic protein include those that (1) have an amino acid sequence that has greater than about 60%, about 65%, about 70%, about 75%, about 80%, about 85%, about 90%, about 91%, about 92%, about 93%, about 94%, about 95%, about 96%, about 97%, about 98% or about 99% or greater amino acid sequence identity, over a region of at least about 25, about 50, about 100, about 200, about 300, about 400, or more amino acids, to a polypeptide encoded by a referenced nucleic acid or an amino acid sequence described herein; and/or (2) specifically bind to antibodies, e.g., polyclonal or monoclonal antibodies, generated against an immunogen comprising a referenced amino acid sequence as described herein, an immunogenic fragment thereof, and/or a conservatively modified variant thereof.

According to the present disclosure, a recombinant protein or polypeptide or peptide includes any proteinaceous molecule obtained via recombinant DNA technology. In some embodiments, natural or wild-type, human, sequences of DLL4 (NM_019074) and/or WNT3A (NM_033131.3) are used.

An "analog," such as a "variant" or a "derivative," is a compound substantially similar in structure and having the same biological activity, albeit in certain instances to a differing degree, to a naturally-occurring molecule. For example, a polypeptide variant refers to a polypeptide sharing substantially similar structure and having the same biological activity as a reference polypeptide. Variants or analogs differ in the composition of their amino acid sequences compared to the naturally-occurring polypeptide from which the analog is derived, based on one or more mutations involving (i) deletion of one or more amino acid residues at one or more termini of the polypeptide and/or one or more internal regions of the naturally-occurring polypeptide sequence (e.g., fragments), (ii) insertion or addition of one or more amino acids at one or more termini (typically an "addition" or "fusion") of the polypeptide and/or one or more internal regions (typically an "insertion") of the naturally-occurring polypeptide sequence or (iii) substitution of one or more amino acids for other amino acids in the naturally-occurring polypeptide sequence. By way of example, a "derivative" is a type of analog and refers to a polypeptide sharing the same or substantially similar structure as a reference polypeptide that has been modified, e.g., chemically.

A variant polypeptide is a type of analog polypeptide and includes insertion variants, wherein one or more amino acid residues are added to a therapeutic protein amino acid sequence of the invention. Insertions may be located at either or both termini of the protein, and/or may be positioned within internal regions of the therapeutic protein amino acid sequence. Insertion variants, with additional residues at either or both termini, include for example, fusion proteins and proteins including amino acid tags or other amino acid labels.

In deletion variants, one or more amino acid residues in a protein or polypeptide as described herein are removed. Deletions can be effected at one or both termini of the therapeutic protein polypeptide, and/or with removal of one or more residues within the therapeutic protein amino acid sequence. Deletion variants, therefore, include fragments of a therapeutic protein polypeptide sequence.

In substitution variants, one or more amino acid residues of a therapeutic protein polypeptide are removed and replaced with alternative residues. In one aspect, the substitutions are conservative in nature and conservative substitutions of this type are well known in the art. Alternatively, the invention embraces substitutions that are also non-conservative. Exemplary conservative substitutions are described in Lehninger, [Biochemistry, 2nd Edition; Worth Publishers, Inc., New York (1975), pp. 71-77].

"Hematopoietic stem cells" are stem cells that develop into other blood cells via a process termed haematopoiesis. Hematopoietic stem cells give rise to different types of blood cells, in lines called myeloid and lymphoid. Myeloid and lymphoid lineages both are involved in dendritic cell formation. Myeloid cells include monocytes, macrophages, neutrophils, basophils, eosinophils, erythrocytes, and megakaryocytes to platelets. Lymphoid cells include T cells, B cells, natural killer cells, and innate lymphoid cells.

HSCs can be found in numerous sources including, but not limited to, bone marrow, umbilical cord and peripheral blood sources. Samples may be taken from each of the aforementioned sources according to methods well known in the art.

HSC transplants are used in the treatment of cancers and other immune system disorders. As described herein, the HSCs, thymic epithelial cells, exosomes and/or T cells provided herein can be used to treat numerous disorders and diseases. In some aspects, the diseases or disorders amenable to treatment by the t methods provided herein are diseases or disorders associated with defective T cells including, but not limited to, X-linked severe combined immunodeficiencies (X-SCIDs), Wiskott-Aldrich syndrome, ataxia telangiectasia, DiGeorge syndrome (22q11.2 deletion syndrome), immuno-osseous dysplasias, dyskeratosis congenita, and chronic mucocutaneous candidiasis, Omenn syndrome, CD40L deficiency and ADA-deficiency. In other aspects, the HSCs, thymic epithelial cells, exosomes and/or T cells provided herein can be used in transplant procedures for hematologic malignancy diseases such as lymphoblastic malignancies such as acute lymphoblastic leukemia, chronic lymphocytic leukemia, lymphomas and multiple myeloma, or myelogenous malignancies such as acute myelogenous leukemia, chronic myelogenous leukemia, myelodysplastic syndromes and the myeloproliferative neoplasms, such as essential thrombocythemia, polycythemia vera and myelofibrosis.

As used herein, the term "expression vector" is synonymous with "vector" and refers to genetic constructs such as a plasmid or virus designed for gene expression in cells. The vector is engineered to contain regulatory sequences that act as enhancer and promoter regions and lead to efficient transcription of the gene carried on the expression vector. By way of example, retroviral expression vectors are contemplated, e.g., pMigR1-HuDLL4:IRES:GFP; NM_019074 and pMNLV-hWNT3A:IRES:GFP; NM_033131.3. As used herein, the term "expressing" is used in the context of protein expression (e.g., from an expression vector). Similarly, the term "display" or "displaying" refers to the presence of an expressed protein (e.g., from an expression vector) or in other aspects the presence of a peptide in the context of a MHC, on the surface of a cell or on the surface membrane of a vesicle such as an exosome.

The cells and exosomes described herein, in some aspects, comprise one expression vector (with respect to a cell) or one recombinant protein expressed from an expression vector (with respect to a cell or an exosome). In additional aspects, a cell or cell line or exosome may comprise more than one expression vector (with respect to a cell) or more than one recombinant protein (e.g., present within the membrane or displayed on a membrane surface, with respect to a cell or exosome). In other aspects, exosomes derived from different cells or cell lines, each with their own distinct expression vector or recombinant protein, are provided in one composition or collection and used in accordance with the methods described herein.

Compositions and therapeutic compositions are also contemplated herein. Also contemplated herein are pharmaceutical compositions and kits containing a cell or collection of cells, or exosome or collection of exosomes, provided herein and one or more components. Pharmaceutical compositions can include cells or exosomes as provided herein and a pharmaceutical carrier. Kits can include the pharmaceutical compositions and/or combinations provided herein, and one or more components, such as instructions for use, a device for administering a compound to a subject, and a device for administering a compound to a subject.

Provided herein are pharmaceutical compositions containing cells or exosomes as provided herein and a suitable pharmaceutical carrier. Pharmaceutical compositions provided herein can be in various forms, e.g., in solid, liquid, powder, aqueous, or lyophilized form. Examples of suitable pharmaceutical carriers are known in the art. Such carriers and/or additives can be formulated by conventional methods and can be administered to the subject at a suitable dose. Stabilizing agents such as lipids, nuclease inhibitors, polymers, and chelating agents can preserve the compositions from degradation within the body.

The cells or exosomes provided herein can be packaged as kits. Kits can optionally include one or more components such as instructions for use, devices, and additional reagents, and components, such as tubes, containers and syringes for practice of the methods.

As used herein, the TEC84 cell line is a cell line produced from a primary culture initiated with a pediatric human thymic tissue using an explant technique as previously described (Schluns K S, Grutkoski P S, Cook J E, Engelmann G L, Le P T. Human thymic epithelial cells produce TGF-beta 3 and express TGF-beta receptors. Int Immunol. 1995; 7:1681-1690.). The established primary TECs were immortalized by infection of the primary cultures with retroviruses containing the HPV E6E7 early genes (from a cell line, PA317 LXSN-16E6E7). The stable TEC lines were selected with G418 (800 µg/ml), expanded in TE media (3:1 DMEM:F12 medium with 5% FCS, 5.5 µg/ml bovine insulin, 0.4 µg/ml hydrocortisone, 9 ng/ml cholera toxin, 0.3% adenine hydrochloride, 1 mM sodium pyruvate, 10 ng/ml epidermal growth factor, 2.5 µg/ml amphotericin B, and 55 ng/ml gentamicin sulfate). The selected TECs (TEC-84) were subjected to four rounds of electronic sorting and expansion for CD104 (integrin ($\beta$4), CD29 (integrin ($\beta$1), and CD49f (VLA6) (See, e.g., Britte C. et al., Experimental Hematology, 39, 570-579 (2011)).

As described herein, the present disclosure provides a method of stimulating production of a T cell from a hematopoietic stem cell. T cells, according to various aspects, will express one or more of CD7, CD3, CD4, and CD8. In other aspects, hematopoietic stem cell will express one or more cell surface marker selected from the group consisting of CD34, CD7 CD127, CD62L CCR9, CCR7, and CXCR4.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a conformation switching probe" includes a plurality of such conformation switching probes and reference to "the microfluidic device" includes reference to one or more microfluidic devices and equivalents thereof known to those skilled in the art, and so forth. It is further noted that the claims may be drafted to exclude any element, e.g., any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. This is intended to provide support for all such combinations.

Example 1

Production and Characterization of Human Thymic Epithelial Cells and Exosomes

This example provides methods for producing human thymic epithelial cells (TECs) genetically engineered to promote T cell development from homing hematopoietic stem cells (HSCs) and exosomes derived from the TECs. The TECs and TEC-derived exosomes are believed to be suitable for applications in the treatment of primary T cell deficiency diseases and enhancing the development of T cells in patients undergoing HSC transplant. As described herein, according to one aspect of the invention, the exosomes may be used as a biological membrane vesicle with a membrane ligand to signal a receptor. Specific examples discussed herein include exosomes capable of signaling the Notch receptor through the human cell surface ligand Delta-like 4 or signaling the Frizzled receptor through WNT3A.

Two human TEC lines were established which were genetically engineered to overexpress human cell surface ligand Delta-like 4 (TEC-DLL4) and WNT3A (TEC-WNT3A), respectively. Exosomes were then generated from these two TEC lines, referred to hereinafter as Exo-DLL4 and Exo-WNT3A, respectively.

As described herein, according to some aspects of the present disclosure the TEC-derived exosomes may be used as reagents for cell-free platform systems for the generation of T cells from HSCs. For example, these systems could be used to initiate the development of T cells in vitro from HSCs collected from bone marrow and umbilical cord blood before giving to patients who are receiving a stem cell transplant to treat hematologic malignancy diseases or to patients with severe immunodeficiency diseases. The utilization of the cell-free platform systems may facilitate the transition of the systems into clinical usage due in part to a reduction of possible contamination of the cell lines with the de novo generated T cells when infusing into patients. Furthermore, it is believed that the exosomes induce a minimal allogeneic response and have a short-half-life in vivo.

A. Generation and Establishment of Human Thymic Epithelial Cell Lines Expressing the Human Notch Ligand Delta-Like 4 (DLL4)

In order to generate and establish the TEC-DLL4, the TEC84 line was transduced with MigR1-GFP retroviral expression vector, either by itself or with the human DLL4 gene incorporated into the expression vector. The TEC-DLL4 line was established after three rounds of electronic sorting for cells that express HLA-A, HLA-B, HLA-C, and DLL4. Expression of these markers was validated by flow cytometric analysis as shown in FIG. 1.

The data demonstrated that the human TEC line that overexpresses human DLL4. DLL4 is readily detectable on the surface of the TEC84-DLL4 (97.7%); the expression of DLL4 on the TEC84 was undetectable. TEC-DLL4 cells is thus able to provide the DLL4 ligand to the Notch receptor and that the DLL4-Notch interaction will induce HSCs to develop into T cells. Further, as discussed below, exosomes secreted by the TEC-DLL4 cells will have DLL4 on the membrane; these exosomes will also be able to bind to Notch on the HSCs and promote T cell development.

B. Characterization of the Extracellular Vesicles from TEC-DLL4 as Exosomes

Extracellular vesicles (EVs) are a natural cellular product; however, they are heterogeneous. Therefore, a subset of EVs, termed exosomes, were isolated and characterized by the expression of the CD63 and CD81 tetraspanins.

Figure 2:
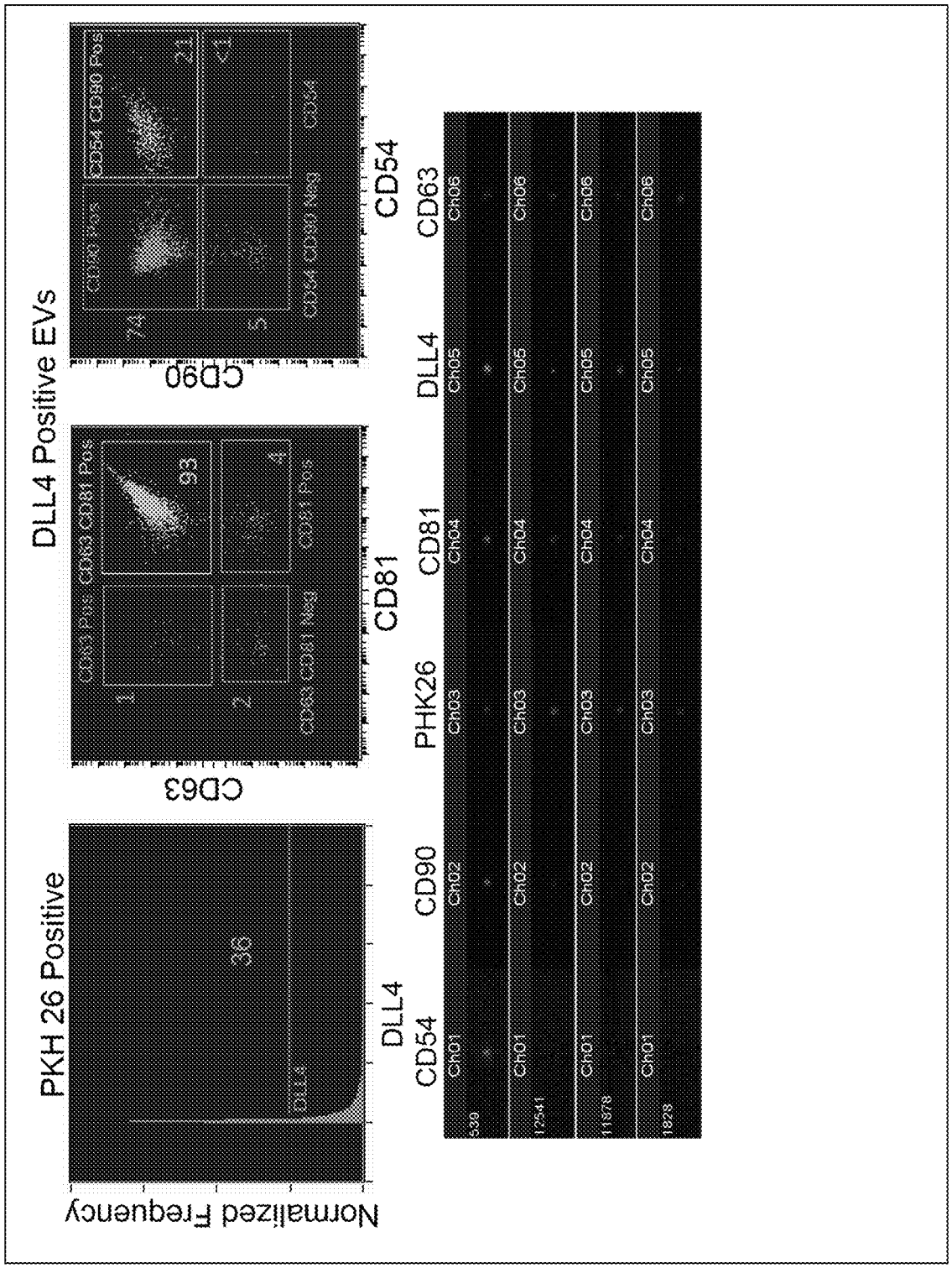
FIG. 2 shows data of analysis of isolated extracellular vesicles (EVs) using an ImmageStream (Amnis). The top panels show that the $DLL4^{pos}$ EVs have both CD63 and CD81 on the surface and therefore are exosomes; the exosomes also have the membrane GPI-anchored protein CD90 and the cell adhesion molecule ICAM-1 (CD54). The lower panels show four representative exosomes (identified by a number on the far left) that express the above-noted surface markers.

Extracellular vesicles (EVs) were purified from TEC-DLL4 culture supernatant using differential centrifugation. EVs were collected as the 100,000×g pellets. Exosomes were identified as EVs that have two tetraspanins on the surface, the CD63 and CD81. As represented in FIG. 2, EVs with surface DLL4 (Top Left) also had surface CD63 and CD81, the two bona fide tetraspanin markers of exosomes (Top Middle). Other surface markers that were also detected were the GPI-anchored protein CD90 and the cell adhesion molecule ICAM-1 (CD54). The lower panel shows the images of a single exosome and the presence of the noted markers.

The data demonstrated the engineered human TEC-DLL4 cell line secretes exosomes with DLL4 (Exo-DLL4) on the membrane, and this is not observed with the parental TEC84 (data not shown). As described herein, the unique Exo-DLL4 could thus be used to identify HSCs that engage Notch signaling and to promote HSCs to develop into T cells.

C. Applications of Exosomes with Membrane DLL4 (Exo-DLL4)

In addition to the above-noted applications of the exosomes, other aspects of the present disclosure include the use of the Exo-DLL4 as membrane reagents to identify cells that engage Notch signaling as described further herein. Notch is a cell membrane receptor that is signaled when binding to its ligands. It was demonstrated that Exo-DLL4 was detectable on the human HSCs identified by the membrane protein CD34. Because Notch signaling is believed to be essential to induce the development of T cells from HSCs, the identification of a subset of the $CD34^{pos}$ HSCs that are able to engage Exo-DLL4 provides an approach and strategy to increase the number of these cells to ameliorate T cell engraftments in patients receiving HSC transplant for the treatment of hematologic malignancy.

Figure 3:
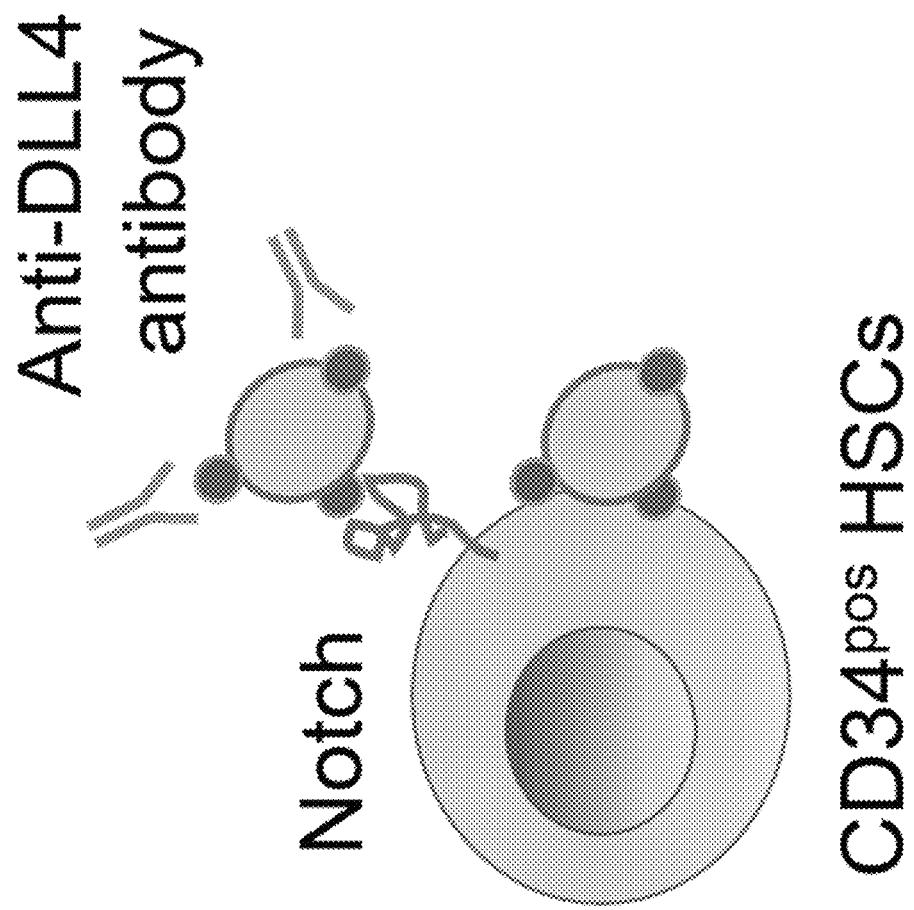
FIG. 3 includes a diagram that illustrates an assay to detect binding of exosomes of TEC-DLL4 (Exo-DLL4) to the Notch receptors expressed on $CD34^{pos}$ hematopoietic stem cells (HSCs).

FIG. 3 illustrates the principle of an assay configured to detect $CD34^{pos}$ HSCs that have Notch receptors engaged with Exo-DLL4. The binding of the Exo-DLL4 to the $CD34^{pos}$ HSCs can be detected with a fluorescence-labeled anti-DLL4 antibody. Since HSCs do not express DLL4, a positive signal would only be detectable when there are Exo-DLL4 on the surface of the HSCs.

Figure 4:
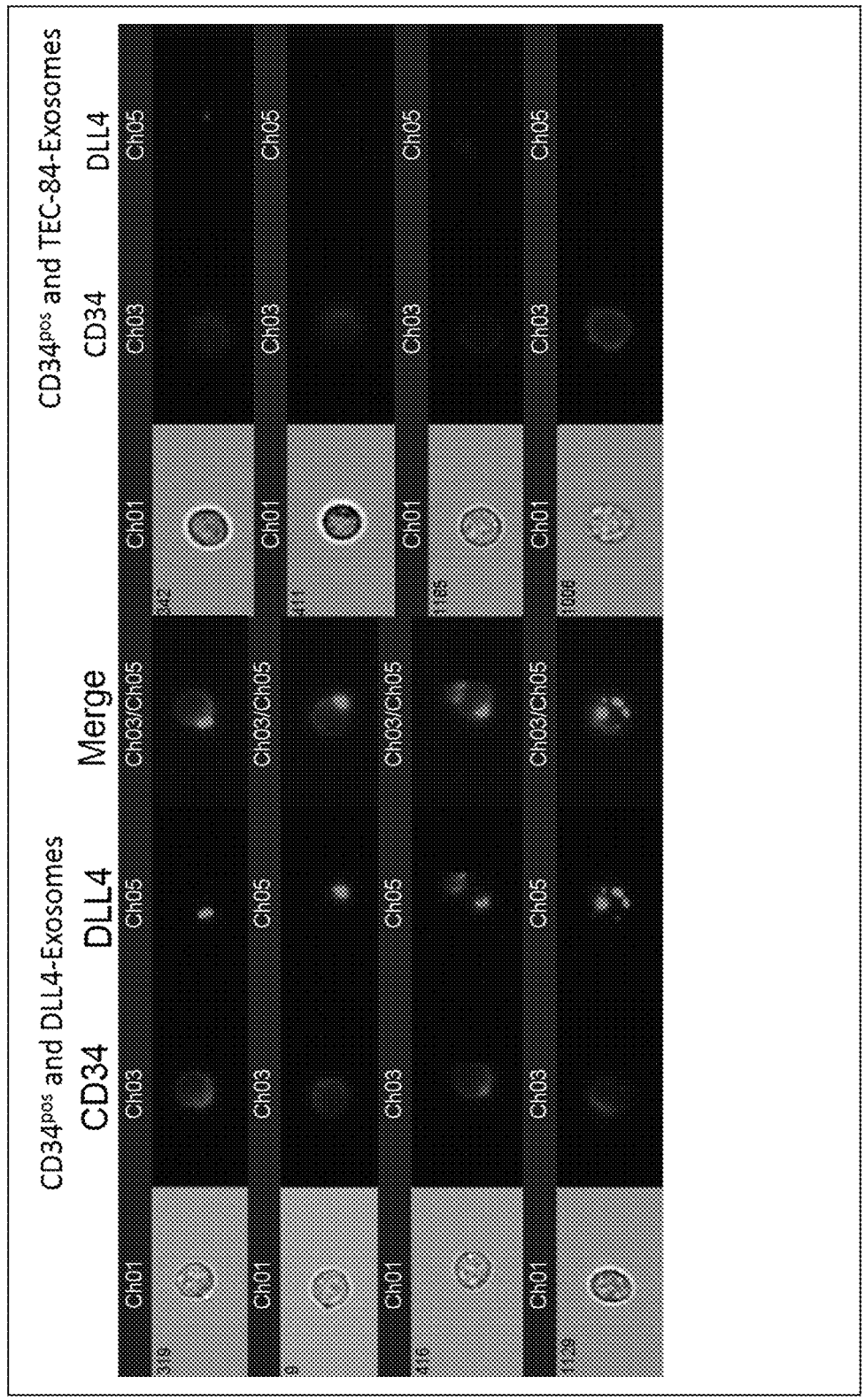
FIG. 4 shows data obtained using the assay of FIG. 3. Exo-DLL4 were detected on $CD34^{pos}$ HSCs (left panels), but not with exosomes from TEC-84 cells. The images show the positive CD34 marker in green, and DLL4 in red. The merge panels show the presence of red Exo-DLL4 on green $CD34^{pos}$ HSCs. Exosomes from TEC-84 were used as controls.

This approach was used to detect Exo-DLL4 on the surface of the $CD34^{pos}$ HSCs as depicted in FIG. 4.

HSCs (1×10$^5$ cells) were centrifuged with the isolated Exo-DLL4 (5×10$^5$ves/mL) at 4000×g at 14° C. for 30 min, and the cells were then stained with CD34 and anti-DLL4 and analyzed by Immagestream analysis (Amnis), a combination of flow cytometry and fluorescent microscopy. The binding of the Exo-DLL4 to Notch on the CD34pos HSCs is detected with a fluorescence-labeled anti-DLL4 antibody. The HSCs do not express DLL4; the positive signal is only detectable when there are Exo-DLL4 on the surface of the HSCs.

The data provided in FIG. 4 indicate that Exo-DLL4s can engage the Notch receptor expressed on HSCs and are detectable. The results also support that this new Exo-DLL4 reagent can be utilized to identify HSCs that engage Notch signaling and thus are the cells that are initiated to develop into T cells.

Figure 5:
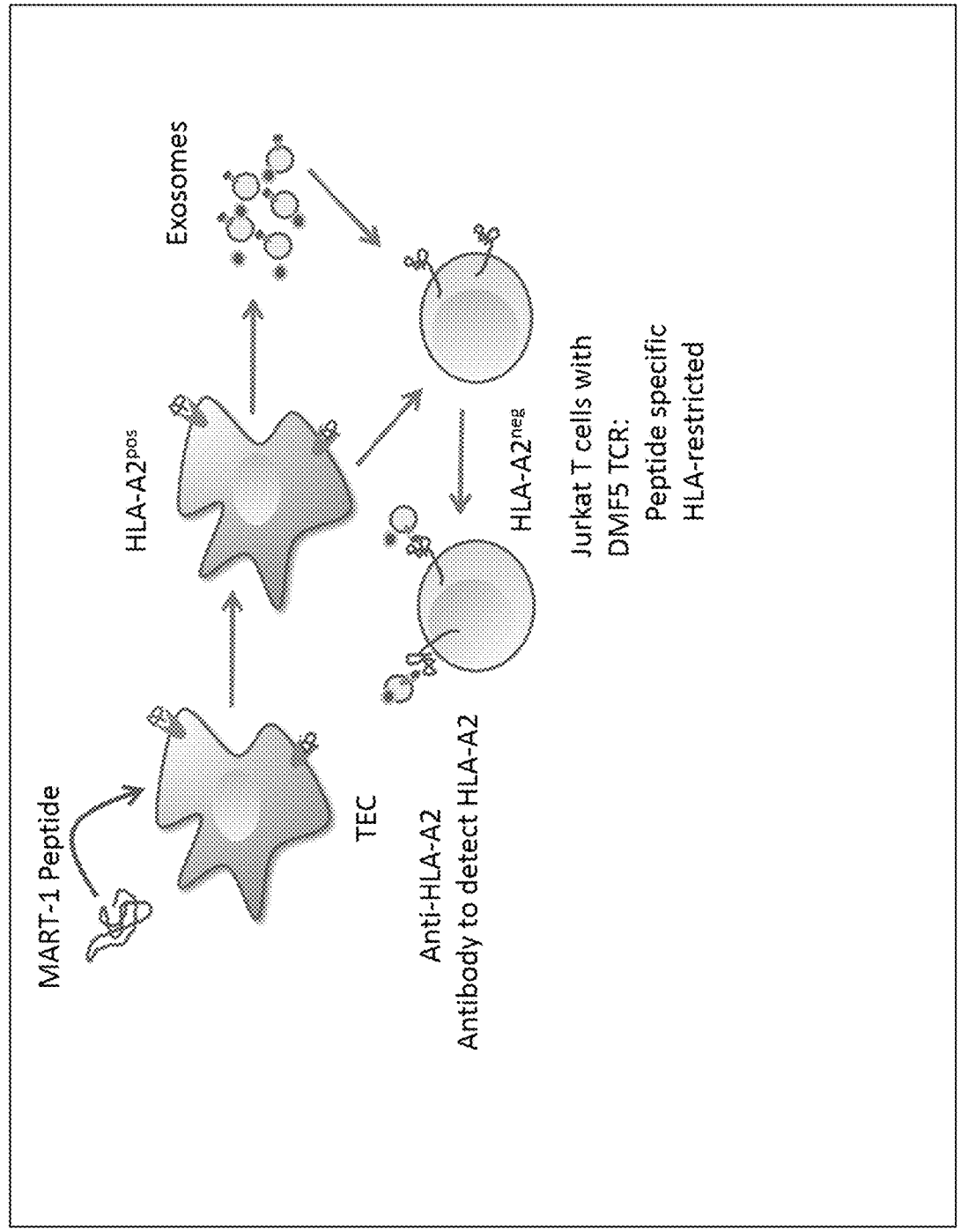
FIG. 5 represents an assay in which TECs having human leukocyte antigen A2 (HLA-A2) (TEC-HLA-A2) were loaded with MART-1 peptide and exosomes were then purified. The isolated exosomes were used to determine if a human Jurkat T cell line expressing the DMF5-TCR specific for MART-1 peptide bind to the exosomes. The presence of the exosomes was detected with an anti-HLA-A2 antibody.

Applying the principle in the assay described above, a strategy to detect T cells expressing a specific T cell receptor (TCR) was developed. In this case, Jurkat T cell line was used that was engineered to express the TCR receptor DMF5 specific for a MART-1 peptide (antigen expressed in skin cancer cells melanoma). The binding of DMF5-TCR to MART-1 peptide occurs only when the MART-1 peptide is complexed with HLA-A2 molecules. FIG. 5 illustrates the experiment.

A TEC84 line that expresses the human HLA-A2 (TEC84-HLA-A2) was generated and the cells were cultured with MART-1 peptide (10 ng/mL) for 48 hrs. The supernatant was then collected, and exosomes were isolated by differential centrifugation as described above section. The isolated exosomes were then mixed with the Jurkat-DMF5 cells ($1\times10^5$ cells) for 30 mins at 14° C. The cells were then stained with an anti-CD3 antibody to identify T cells, CD34 antibody to detect the TCR-DMF5, and anti-HLA-2 antibody to detect the exosomes.

Figure 6:
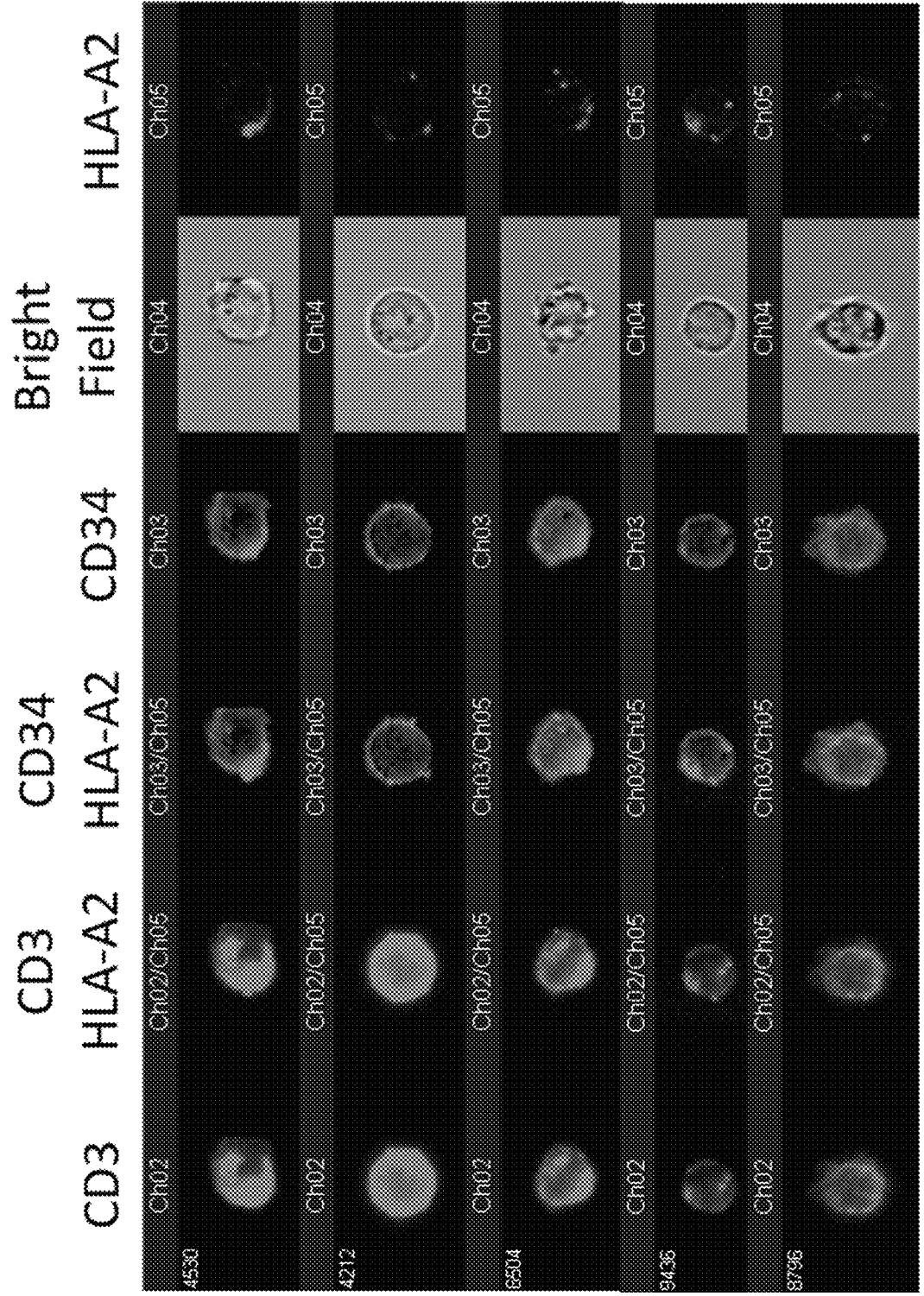
FIG. 6 shows data obtained from the assay of FIG. 5.
Figure 7:
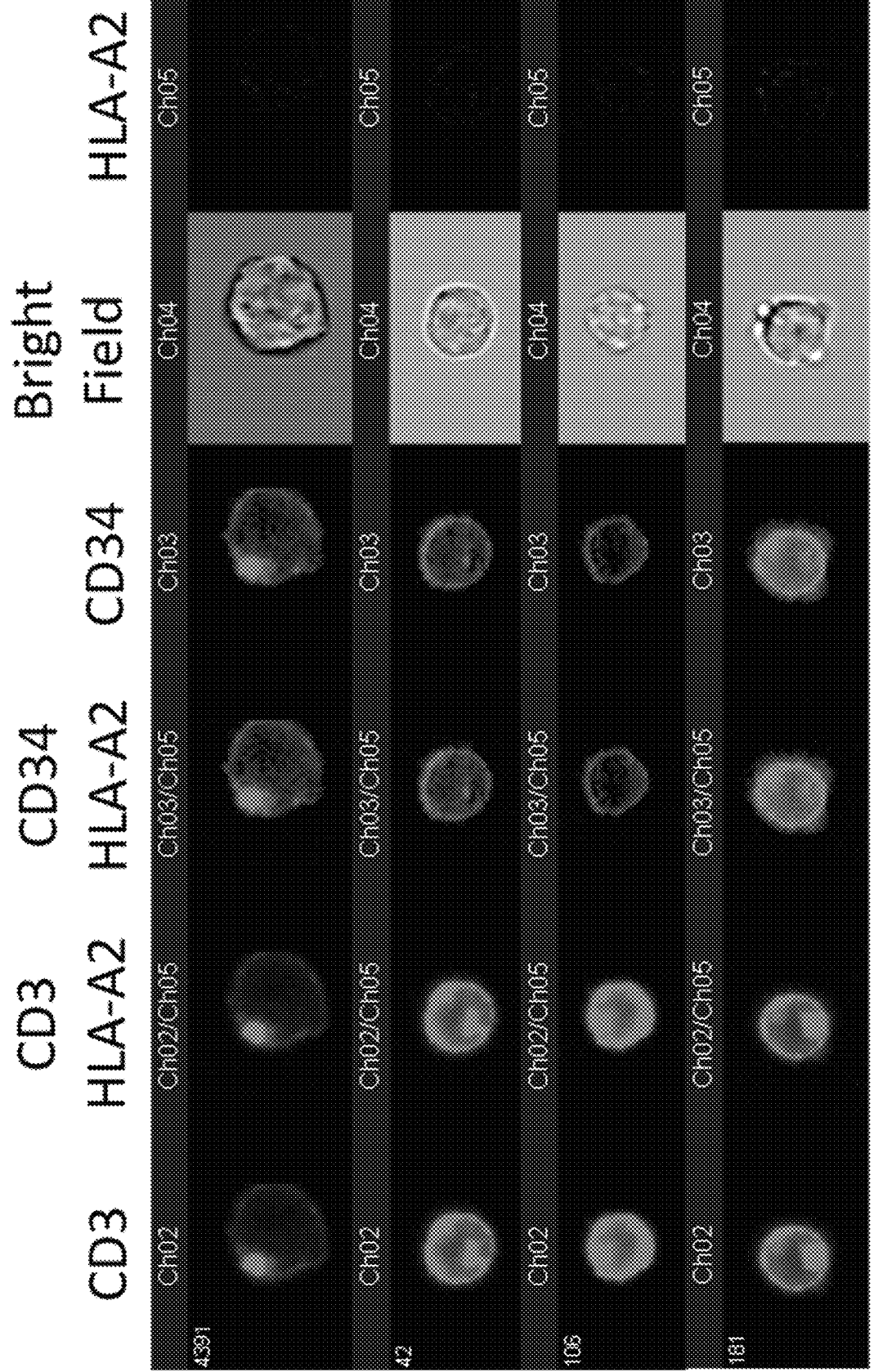
FIG. 7 shows that exosomes isolated from TEC-HLA-A2 not loaded with MART-1 peptide show no binding to Jurkat cells and no detectable HLA-A2.

Binding of exosomes-HLA-A2 to the Jurkat DMF5 T cells only occurred when MART-1 peptides were loaded into TEC-HLA-A2 (FIG. 6). Exosomes isolated from TEC-HLA-A2 without MART-1 antigen showed no binding to the Jurkat cells and no detectable HLA-A2 (FIG. 7). Thus, exosomes secreted from TEC carry the loaded peptide, and T cells with TCR specific for the peptide can bind to the peptide in an MHC-restriction fashion.

The following Examples build on the above disclosure and provide additional embodiments, as described herein.

Example 2

Figure 8:
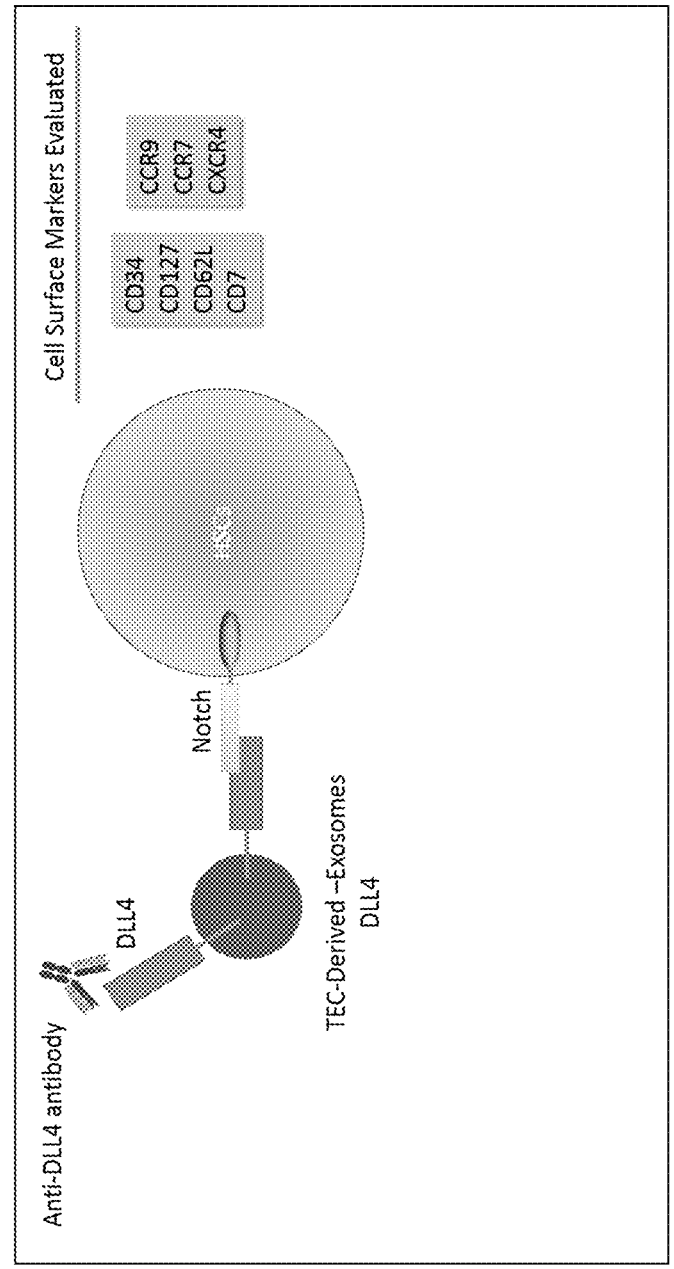
FIG. 8 shows an assay to detect Exo-DLL4 on the surface of target cells. Isolated Exo-DLL4 were allowed to bind to HSCs at 14° C. for 15 min. HSCs that engage Exo-DLL4 were analyzed using an antibody specific for DLL4 and other cells surface markers by flow cytometric analysis. The two rectangular boxes list the cell surface markers that were evaluated.

Exosomes from TEC-DLL4 Cells are a Novel and Unique Reagent to Identify a Fraction of Human Hematopoietic Stem Cells As described above, human thymic epithelial cells (TECs) were engineered to overexpress the membrane Delta-like 4 (DLL4, a ligand for the Notch receptor) and demonstrated that exosomes derived from the TEC-DLL4 line display DLL4 on the surface membrane of the exosomes (Exo-DLL4). The exosomes can thus be utilized to identify cells that express the Notch receptor and engage the ligand. An assay that allows identifying the Exo-DLL4 engaged cells is also contemplated. FIG. 8 depicts one such exemplary assay.

In this assay, HSCs $1\times10^5$-$3\times10^5$ are mixed with isolated exosomes ($5\times10^5$ vesicles/mL) then centrifuged at 4000×g for 30 mins at 14° C. The cells are then washed and then stained with a cocktail of directly conjugated antibodies. The stained cells are analyzed by flow cytometry or by the ImmageStream (Amnis).

Using the assay described in FIG. 8, the following embodiments were discovered.

Figure 9:
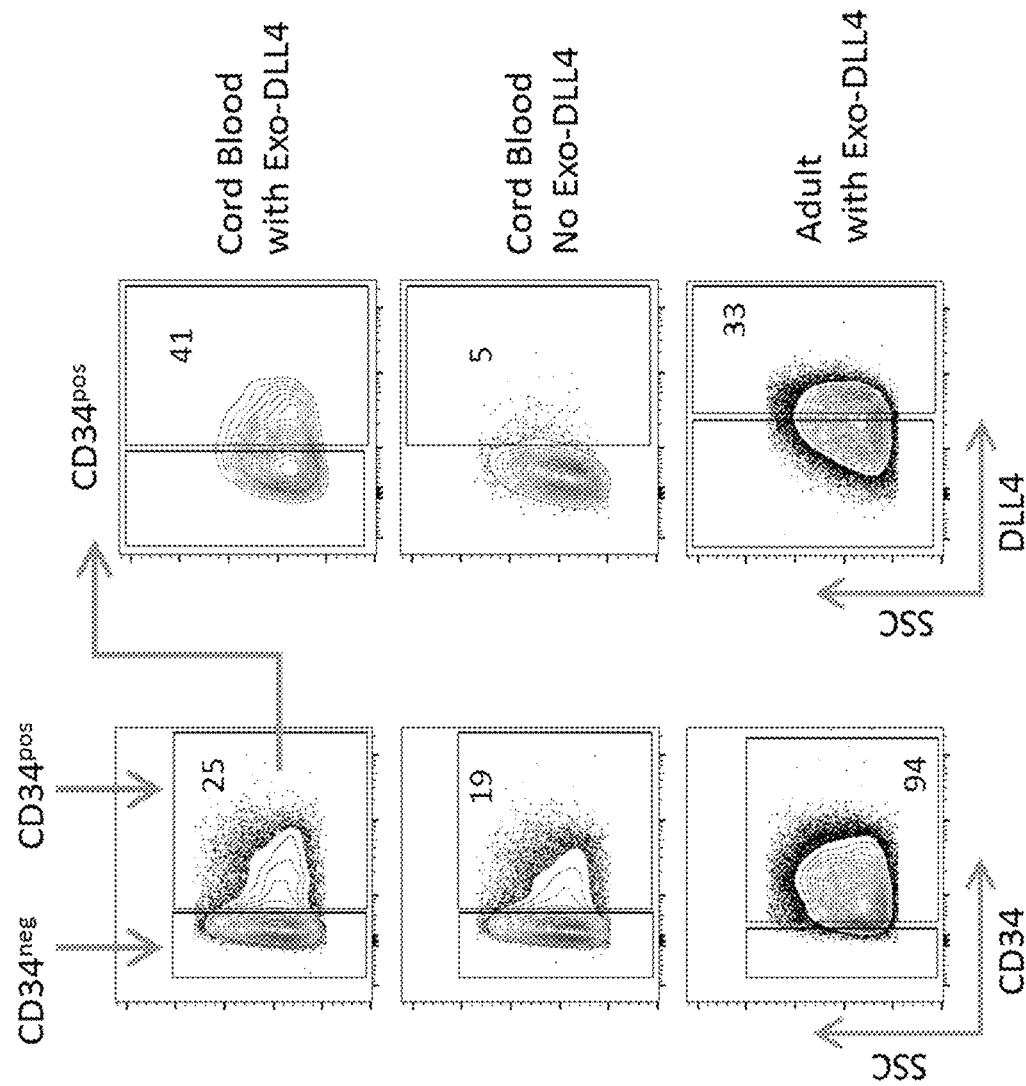
FIG. 9 shows that Exo-DLL4 bind to and were detectable on a subset of $CD34^{pos}$ HSCs.

A. Only a Fraction of the HSC Population Shows Detectable Exo-DLL4 on the Cell Surface FIG. 9 shows that Exo-DLL4 bind to and were detectable on a subset of CD34pos HSCs. Two sources of human HSCs were used, the umbilical cord blood HSCs and mobilized adult peripheral HSCs. Cells were analyzed using flow cytometry. The middle panels depict cells treated with no Exo-DLL4 (control), indicating that detectable surface DLL4 only occurs when cells are incubated with Exo-DLL4. Numbers represent the percent of cells expressing the analyzed markers.

B. Exo-DLL4 Identifies a Unique Subset of HSCs Distinct from the Subset of HSCs with No Detectable Exo-DLL4

Whether a population of HSCs with detectable Exo-DLL4 (Exo-DLL4Pos) is distinct from HSCs that do not engage Exo-DLL4 (Exo-DLL4Neg HSCs) was next determined. This was evaluated based on the expression of the following cell surface molecules: CD34, CD7, CD62L, CD127, CCR9, CCR7, and CXCR4.

Figure 10A:
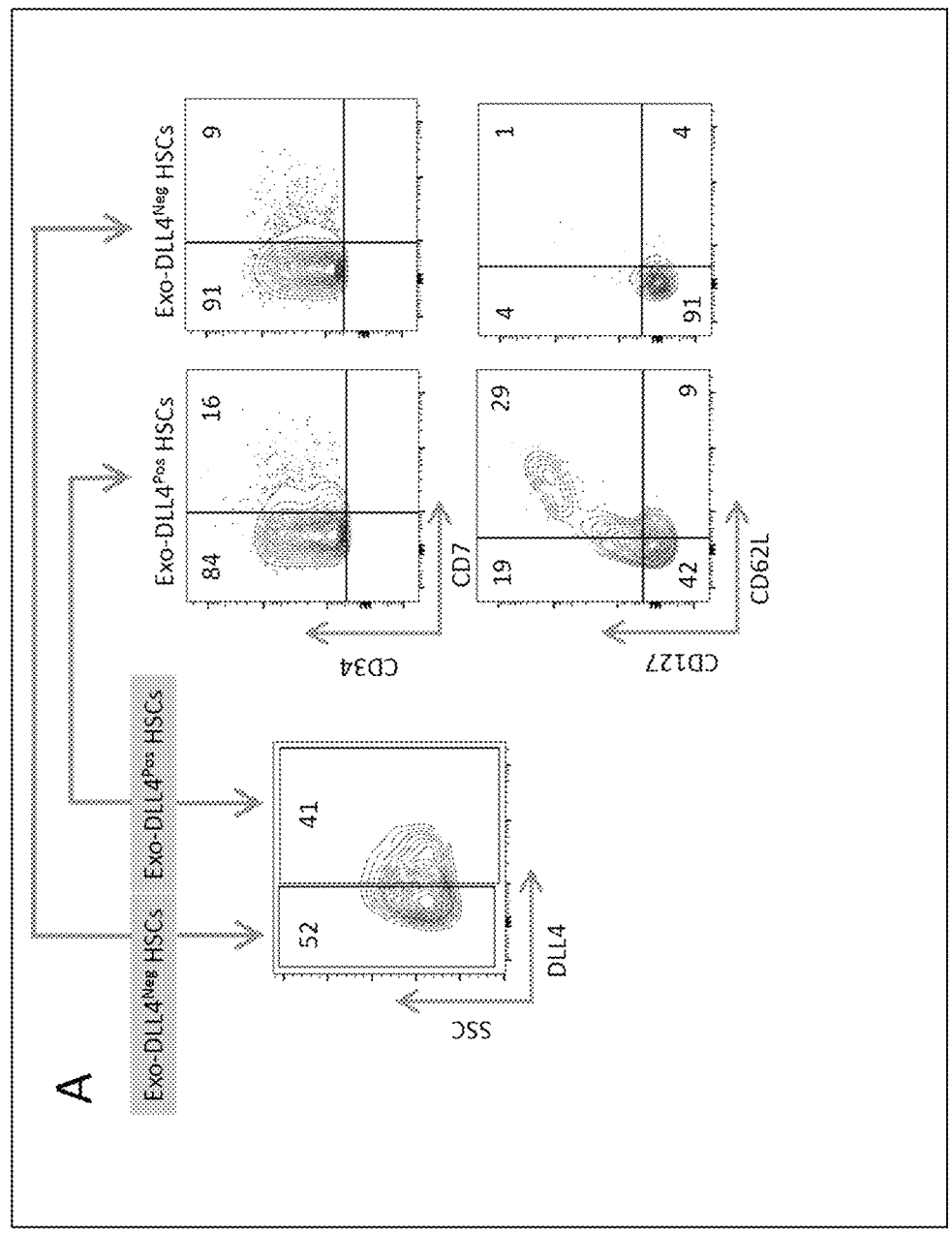
FIG. 10A shows detection of CD127 and CD62L expression in the $CD7^{Pos}$ populations within the Exo-DLL4$^{Pos}$ and Exo-DLL4$^{Neg}$ HSCs from umbilical cord blood. Numbers represent the percent of cells expressing the analyzed markers.

The discovery that Exo-DLL4$^{Pos}$ HSCs predominantly express the chemokine receptors CCR9, CCR7, and CXCR4 as compared to the Exo-DLL4Neg HSC subset, indicates that these cells have the potential and capacity to be recruited into the thymus in responding to their cognate chemokines. In FIG. 10A, the data demonstrate that while both the Exo-DLL4$^{Neg}$ and Exo-DLL4$^{Pos}$ HSC populations have CD7Pos cells, the CD7$^{Pos}$ population in the Exo-DLL4$^{Pos}$ HSCs express CD127 and CD62L. In contrast, the CD7$^{Pos}$ population from Exo-DLL4$^{Neg}$ does not express CD127 and CD62L.

Figure 10B:
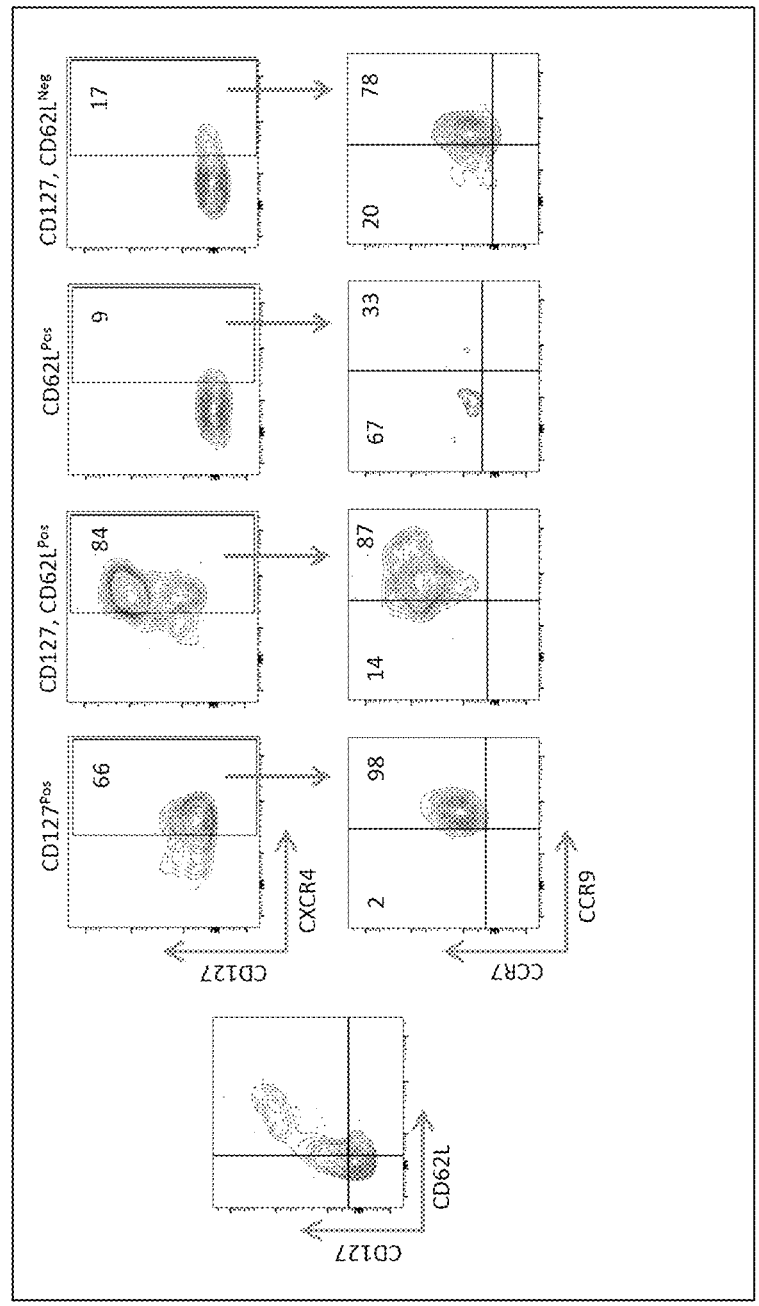
FIG. 10B shows expression of chemokine receptors CXCR4, CCR7 and CCR9 in the Exo-DLL4Pos HSCs. Numbers represent the percent of cells expressing the analyzed markers.

The cell populations identified by the expression of CD127 and CD62L were further analyzed for the expression of the three chemokine receptors. These populations are defined as CD127$^{Pos}$, CD62L CD127$^{Pos}$, CD62L$^{Pos}$, and CD62L CD127$^{Neg}$. The data in FIG. 10B clearly show that the CD62 CD127Pos population display a unique pattern of expression for the chemokine receptors CXCR4, CCR7, and CCR9.

Figure 11:
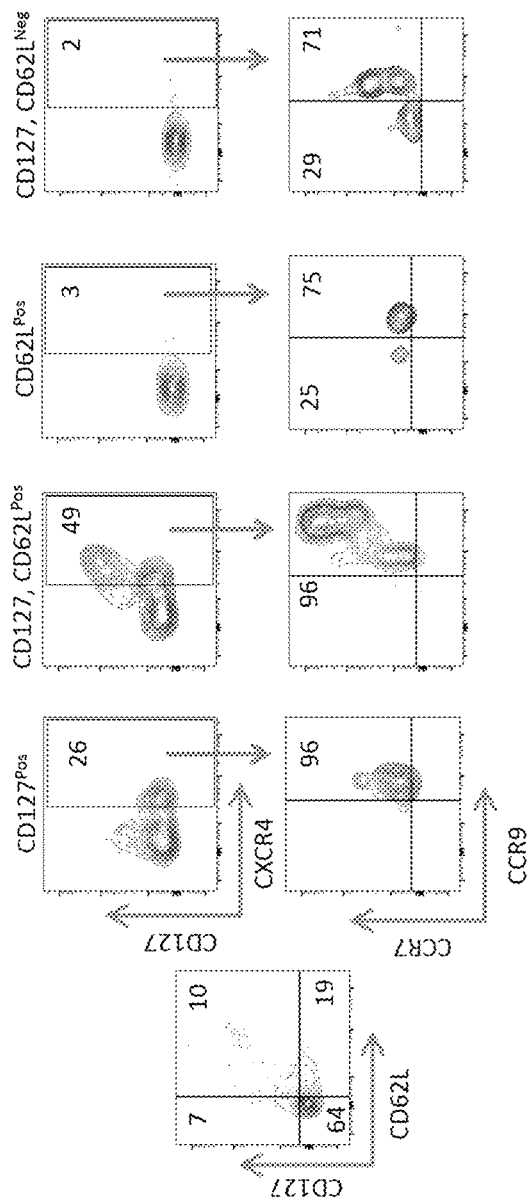
FIG. 11 shows the characterization of Exo-DLL4Pos HSCs from mobilized adult peripheral blood. Numbers represent the percent of cells expressing the analyzed markers.

The expression patterns of CD7, CD127, CD62L, CXCR4, CCR7, and CCR9 are also found in the isolated mobilized adult peripheral blood, showing identical patterns (FIG. 11).

Thus, as show herein, the engineered Exo-DLL4 can bind to HSCs and is detected on the surface of the HSCs. The identification of the HSCs that engage Exo-DLL4 allows the further characterization of these cells. The data indicate that these HSC-Exo-DLL4POS cells are identified as a subset of the CD34$^{pos}$ that also express CD7, CD127, CD62L, CXCR4, CCR7, and CCR9. Since this subset engages DLL4, they would be the prime target cells to commit to developing into T cells. The data further indicate that the identification of this subset will facilitate the monitoring of the number of these cells within a donor sample, which provides useful data to anticipate transplant outcomes, in the context of T cell engraftment. Having identification of this subset also facilitate new strategy, methodologies to increase the number to enhance T cell engraftment.

This Example therefore supports the following exemplary embodiments: 1. Exo-DLL4 is a unique reagent that is a product of the engineered human thymic epithelial cell line (TEC-DLL4); 2. the assay utilizing Exo-DLL4 can identify a fraction of HSCs from umbilical cord blood and mobilized peripheral blood based on the ability of HSCs to bind to Exo-DLL4; 3. the assay and Exo-DLL4 can identify HSCs with a unique expression of cell surface markers and these cells are anticipated to be recruited into the thymus—termed Thymic Seeding Cells or TSCs; 4. Exo-DLL4 is a reagent to monitor TSC levels in HSCs and predict the potential of HSCs to generate T cells upon HSC transplant; and 5. Exo-DLL4 is a reagent to enrich for TSCs in HSCs for transplant.

Example 3

Development of a Cell-Free System with Exo-DLL4 to Promote T Lineage Commitment and Development of HSCs Having demonstrated that the Exo-DLL4 are capable of binding to a subset of HSCs with unique surface phenotypes, their activity in promoting T lineage commitment and development was next tested.

HSCs (2×10⁴) were cultured with Exo-DLL4 with a predetermined concentration for up to 4 weeks, and the presence of developing T cells was evaluated based on the expression of CD7, CD3, CD4, and CD8 using flow cytometry. The culture medium contains the following cytokines: SCF, FLT3L, TPO (all at 50 ng/mL), and IL7 (10 ng/mL). Developing T cells are harvested weekly for analysis; cells are reseeded with fresh medium with cytokines. After the third week, in addition to the above cytokines, IL15 at 10 ng/mL is added to the culture. For the data shown in FIG. 12, exosomes were from TEC84, TEC-WNT3A, and TEC-DLL4 or a combined TEC-WNT3A and TEC-DLL4. Here, the function of the TEC-WNT3A-derived exosome was also. The engineered TEC-WNT3A was established from the parental TEC84.

Figure 12:
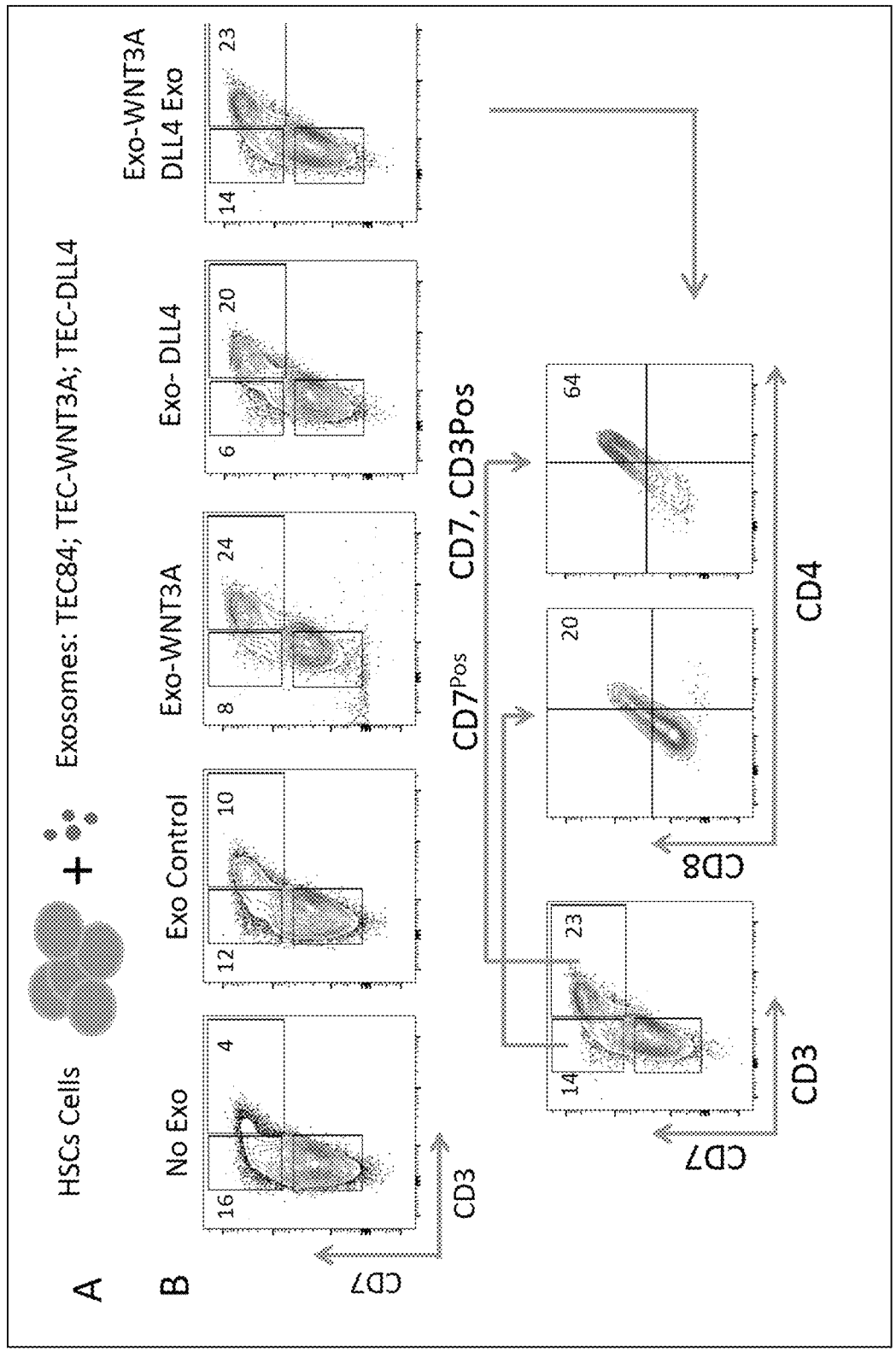
FIG. 12 shows Exo-DLL4 and Exo-WNT3A are able to promote HSCs from cord blood to committee to T lineage and develop in to immature T cells development. Analysis was performed after one week in culture. A. Diagram describes the experiment; B. Analysis for the expression of CD7 and CD3 and the expression of CD4 and CD8 within the CD7 CD3Pos population. Numbers represent the percent of cells expressing the analyzed markers.

As seen in FIG. 12, the CD7, CD3$^{Pos}$ emerged from HSCs after one week in culture; analysis of the CD7 CD3$^{Pos}$ cells revealed that they also express both CD4 and CD8, indicating that they are the developing immature double-positive T cells.

Figure 13:
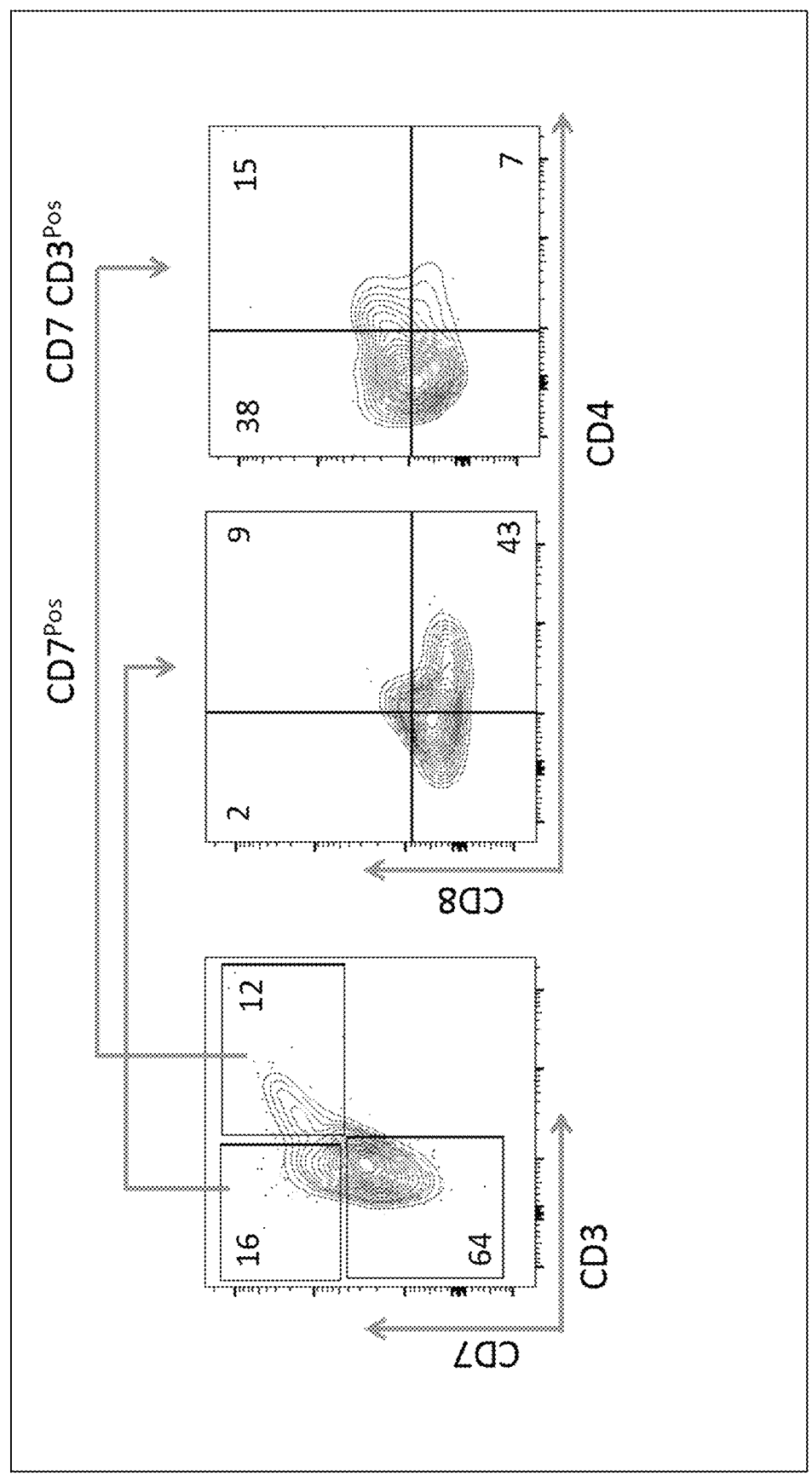
FIG. 13 shows the generation of Single CD4 and CD8 T cells from HSCs after 2 weeks in culture. Numbers represent the percent of cells expressing the analyzed markers.

After 2 weeks in culture, the presence of the mature single CD4 and CD8 T cells were detected, indicating that the Exo-DLL4 are functional and capable of promoting HSCs to develop into CD7, CD3 CD4Pos and CD7, CD3, and CD8Pos T cells in vitro (FIG. 13).

Thus, as show herein, the data demonstrate that the Exo-DLL4 and Exo-WNT3A are functional in promoting HSCs to develop into T cells, establishing that a cell-free system is feasible with the utilization of exosomes from engineered TEC84 cells. This Example therefore supports the following exemplary embodiments: 1. The Exo-DLL4 isolated from TEC-DLL4 are biologically active in promoting HSCs to commit and differentiate into CD7$^{Pos}$, CD7 CD3$^{Pos}$, immature CD4 CD8 double-positive, and mature single CD4$^{Pos}$ or CD8$^{Pos}$ T cells; 2. The Exo-DLL4 could be utilized in a cell-free culture system to promote the generation of T cells from HSCs; 3. The Exo-DLL4 could be utilized to prime HSCs to promote T lineage commitment; this is clinically relevant in the context of HSC transplant; and 4. The generated pool of the immature CD4 CD8 double-positive T cells could serve as a heterogeneous pool of T cells from which T cells with a specific T cell receptor specificity and Human Leukocyte Antigen (HLA) restriction could be selected (as described further herein).

Example 4

Exo-DLL4 is a Novel Reagent to Identify and Select T Cells with a Specific T Cell Receptor and HLA Restriction As shown above, the exosomes from the TEC lines are a source of exosomes that can be loaded with a specific antigenic peptide and presented by a particular HLA. The reagent then can be used to identify T cells with the specificity for the peptide and is restricted by the selected HLA. See, for example, Example 1 and FIGS. 5-7, herein.

Figure 14:
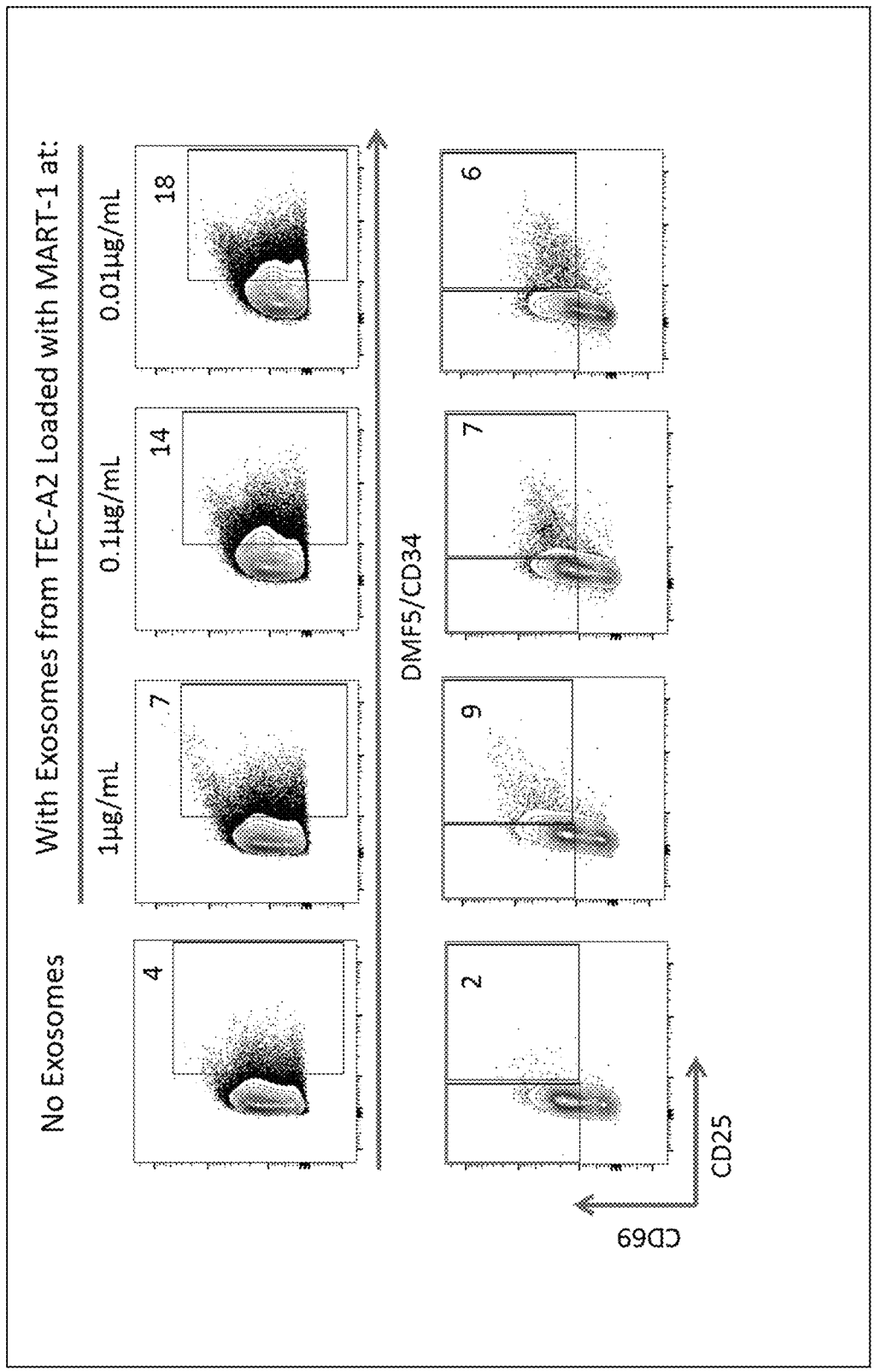
FIG. 14 shows exosomes with HLA-A2 and MART-1 peptide activate Jurkat T cells express the DMF5 T cell receptors. The activated T express both CD25 and CD69 activation markers. Numbers represent the percent of cells expressing the analyzed markers.

FIG. 14 shows data demonstrating exosomes loaded with peptide are functional. T cells cultured without exosomes displayed low levels of expression for the two activation markers CD25 and CD69. However, T cells cultured with exosomes loaded with MART-1 peptide showed an increase in the percent of cells expressing the TCR-DMF5 and expression of CD25 and CD69 (FIG. 14).

Thus, exosomes loaded with a specific peptide presented with one particular HLA could be used to promote maturation of specific T cells from the double-positive immature T cell pool, generated using Exo-DLL4. This Example therefore supports the following exemplary embodiments: 1. Exosomes from TEC84 cells can be engineered to express a specific HLA antigen (the example here is HLA-A2); 2. When loaded with peptides, the TEC secrete exosomes with peptides that can be used to detect T cells with a specific T cell receptor specificity and HLA restriction; and 3. The peptide-loaded exosomes are functionally active and can be used to activate T cells; the functional capacity is essential to promote differentiation and maturation of the double-positive immature T cells.

Example 5

Characterization of TEC-DLL4 Cell Line and Subclones

Additional experiments were performed to provide additional data demonstrating the uniqueness of the TEC-DLL4 cell line and the derivative clones. Because signaling of the Notch receptor is mediated by DLL4, the density of DLL4 on the cell surface can critically contribute to its function in initiating T cell development.

A limiting dilution analysis was performed to establish clones from the parental TEC-DLL4 line. Thirteen clones were selected and evaluated for the expression and densities of surface DLL4; the densities are measured by the mean fluorescence intensity or MFI using flow cytometry. The forward scatter (FSC) and Side Scatter (SSC) measure cell size and cellular morphology, respectively, of the clones. In Table 1, the 13 clones are categorized based on the densities of surface DLL4:

TABLE 1

| Clone ID | Names | FSC | MFI SSC | DLL4 |
| --- | --- | --- | --- | --- |
| 10 | G7 | 90176 | 53056 | 70019 |
| 5 | E9 | 84864 | 53504 | 54614 |
| 12 | G5 | 89280 | 52544 | 51647 |
| 9 | G10 | 92096 | 60096 | 42342 |
| 2 | B5 | 62114 | 62592 | 38723 |
| 7 | H2 | 80832 | 52288 | 35082 |
| 11 | C4 | 83264 | 64704 | 14021 |
| 4 | E8 | 92864 | 71936 | 13265 |
| 1 | B10 | 83776 | 61120 | 12073 |
| 8 | H9 | 93248 | 60928 | 10675 |
| 3 | C8 | 88512 | 59200 | 7957 |
| 13 | G3 | 95104 | 69504 | 5787 |
| 6 | E12 | 90752 | 63613 | 2998 |

These clones were tested for their ability to promote the growth of the HSCs. HSCs (3×10⁴ cells) were cultured with each the TEC-DLL4 clones (seeded at 5×10⁴ cells/well 2 days before the addition of HSCs). Table 2 shows the classification of these clones on their ability to expand the total cellularity after three weeks in culture. After each week, the total numbers of cells were counted, and fold-expansion was calculated as the ratios of input/output. The overall expansion was calculated by multiplying the expansion of week 1-3.

TABLE 2

| Clone | | Cell Numbers | | | | | | Total |
|---|---|---|---|---|---|---|---|---|
| | | 1st week | | 2nd week | | 3rd week | | |
| ID | Names | Number | x-Fold | Number | x-Fold | Number | x-Fold | Expansion |
| 9 | G10 | 8.00E+05 | 13 | 1.60E+06 | 80 | 6.00E+05 | 30 | 32000 |
| 10 | G7 | 1.00E+06 | 17 | 8.00E+05 | 40 | 8.00E+05 | 40 | 26667 |
| 11 | C4 | 1.40E+06 | 23 | 8.00E+05 | 40 | 4.00E+05 | 20 | 18667 |
| 4 | E8 | 8.00E+05 | 13 | 6.00E+05 | 30 | 5.00E+05 | 25 | 10000 |
| 3 | C8 | 6.00E+05 | 10 | 4.00E+05 | 20 | 6.00E+05 | 30 | 6000 |
| 6 | E12 | 6.00E+05 | 10 | 8.00E+05 | 40 | 2.00E+05 | 10 | 4000 |
| 8 | H9 | 3.00E+05 | 5 | 8.00E+05 | 40 | 4.00E+05 | 20 | 4000 |
| 12 | G5 | 2.00E+05 | 3 | 8.00E+05 | 40 | 5.00E+05 | 25 | 3333 |
| 13 | G3 | 3.00E+05 | 5 | 6.00E+05 | 30 | 4.00E+05 | 20 | 3000 |
| 1 | B10 | 3.00E+05 | 5 | 4.00E+05 | 20 | 4.00E+05 | 20 | 2000 |
| 5 | E9 | 2.00E+05 | 3 | 5.00E+05 | 25 | 3.00E+05 | 15 | 1250 |
| 7 | H2 | 2.00E+05 | 3 | 4.00E+05 | 20 | 3.00E+05 | 15 | 1000 |
| 2 | B5 | 6.00E+04 | 1 | 3.00E+05 | 15 | 6.00E+05 | 30 | 450 |

Thus, the density of DLL4 and the ability to promote cellular expansion define the uniqueness of the TEC-DLL4 and its derivative clones. The data indicate the TEC-DLL4 line is unique and be categorized further based on the density of DLL4 on the cell surface. The clones are individual cellular sources from which exosomes could be generated. The ability of specific clones with a high capacity of inducing HSC expansion would be valuable reagent to increase the number of HSCs for transplant. This Example therefore supports the following exemplary embodiments: 1. The established clones can be used to genetically identify novel genes or novel function of known genes in promoting HSCs to develop into T cells; and 2. Functional activities of the clones and their exosomes support HSCs development which include promoting cellular proliferation, T lineage commitment, and differentiation into mature T cells.

What is claimed is:

1. An isolated human thymic epithelial cell comprising at least one expression vector encoding a human Delta-like 4 gene (DLL4), wherein said expression vector is capable of expressing a Delta-like 4 protein, wherein said cell is capable of producing an exosome which displays human Delta-like 4 protein on its membrane surface, and wherein said exosome is capable of promoting T cell development from hematopoietic stem cell (HSC).

2. The isolated cell of claim 1 wherein the Delta-like 4 protein amino acid sequence is the natural human amino acid sequence or is a fragment, analog or derivative of the natural human amino acid sequence.

3. The isolated cell of claim 2 wherein said cell is a genetically modified cell from cell line TEC84.

4. A composition comprising a collection of cells comprising a cell line comprised of isolated human thymic epithelial cell according to claim 1.

5. An isolated human thymic epithelial cell comprising at least one expression vector encoding a human Delta-like 4 gene (DLL4), wherein said expression vector is capable of expressing a Delta-like 4 protein, wherein said cell is capable of producing an exosome which displays human Delta-like 4 protein on its membrane surface, wherein said exosome binds to $CD34^{POS}$ HSCs, and wherein said exosome expresses CD7, CD127, CD62L, CXCR4, CCR7, and CCR9.

6. An isolated human thymic epithelial cell comprising at least one expression vector encoding a human Delta-like 4 gene (DLL4), wherein said expression vector is capable of expressing a Delta-like 4 protein, wherein said cell is capable of producing an exosome which displays human Delta-like 4 protein on its membrane surface, wherein said exosome promotes HSCs to commit and differentiate into CD7+, CD7 CD3+, immature CD4 CD8 double-positive, and mature single CD4+ or CD8+ T cells.

7. An isolated human thymic epithelial cell comprising at least one expression vector encoding a human Delta-like 4 gene (DLL4), wherein said expression vector is capable of expressing a Delta-like 4 protein, wherein said cell is capable of producing an exosome which displays human Delta-like 4 protein on its membrane surface, wherein said exosome expresses a human leukocyte antigen (HLA) and an antigenic peptide.

8. The isolated human thymic epithelial cell of claim 7, wherein the HLA is HLA-A2 and wherein the antigenic peptide is MART-1.

* * * * *